US009127299B2

(12) United States Patent
Hölker et al.

(10) Patent No.: US 9,127,299 B2
(45) Date of Patent: Sep. 8, 2015

(54) DIRECTED SELECTIVE SOLID-PHASE CULTURING OF STABLE MICROBIAL MIXED POPULATIONS FOR THE CONTINUOUS PREPARATION OF DEFINED ENZYME AND METABOLITE MIXTURES

(75) Inventors: Udo Hölker, Königswinter-Rauschendorf (DE); Martina Janssen, Königswinter-Rauschendorf (DE); Jürgen Lenz, Alfter (DE)

(73) Assignee: SENZYME GMBH (DE)

( * ) Notice: Subject to any disclaimer, the term of this patent is extended or adjusted under 35 U.S.C. 154(b) by 1183 days.

(21) Appl. No.: 10/562,248

(22) PCT Filed: Jun. 24, 2004

(86) PCT No.: PCT/EP2004/051234
§ 371 (c)(1),
(2), (4) Date: Oct. 27, 2006

(87) PCT Pub. No.: WO2004/113490
PCT Pub. Date: Dec. 29, 2004

(65) Prior Publication Data
US 2007/0048852 A1 Mar. 1, 2007

(30) Foreign Application Priority Data

Jun. 24, 2003 (DE) .................................. 103 28 552
Feb. 25, 2004 (DE) ........................ 10 2004 009 161

(51) Int. Cl.
| | | |
|---|---|---|
| C12P 1/02 | (2006.01) | |
| C12P 39/00 | (2006.01) | |
| C12M 1/107 | (2006.01) | |
| C12M 1/00 | (2006.01) | |
| C12M 1/16 | (2006.01) | |
| C12M 1/06 | (2006.01) | |
| C12M 1/26 | (2006.01) | |
| C12M 1/34 | (2006.01) | |
| C12N 1/14 | (2006.01) | |
| C12N 1/38 | (2006.01) | |
| C12N 9/02 | (2006.01) | |
| C12N 9/26 | (2006.01) | |
| C12N 9/42 | (2006.01) | |
| C12N 9/24 | (2006.01) | |

(52) U.S. Cl.
CPC ................ *C12P 39/00* (2013.01); *C12M 21/04* (2013.01); *C12M 21/14* (2013.01); *C12M 21/16* (2013.01); *C12M 27/06* (2013.01); *C12M 33/16* (2013.01); *C12M 33/18* (2013.01); *C12M 33/20* (2013.01); *C12M 41/12* (2013.01); *C12M 41/26* (2013.01); *C12M 41/28* (2013.01); *C12M 41/32* (2013.01); *C12M 41/34* (2013.01); *C12N 1/14* (2013.01); *C12N 1/38* (2013.01); *C12N 9/0004* (2013.01); *C12N 9/248* (2013.01); *C12N 9/2411* (2013.01); *C12N 9/2437* (2013.01); *Y02E 50/343* (2013.01)

(58) Field of Classification Search
None
See application file for complete search history.

(56) References Cited

U.S. PATENT DOCUMENTS 5,773,526 A 6/1998 Van Dijk et al. .............. 210/603
6,485,952 B1 * 11/2002 Bradley et al. ................ 435/195

FOREIGN PATENT DOCUMENTS

| DE | 4119798 | 12/1992 |
|---|---|---|
| DE | 29520618 | 5/1996 |
| DE | 19624268 | 4/1997 |
| EP | 0140723 | 5/1985 |
| EP | 0225479 | 11/1986 |
| EP | 1258741 | 5/2002 |
| WO | WO02/088342 | 11/2002 |
| WO | WO 02/100999 A2 * | 12/2002 |

OTHER PUBLICATIONS

NCBI Taxonomy search results for *Aspergillus niger*.*
Durand, A., Biochemical Engineering Journal, Mar. 2003, vol. 13, p. 113-125.*
Tengerdy et al., Biochemical Engineering Journal, Mar. 2003, vol. 13, p. 169-179.*
Pandey et al., Process Biochemistry, 2000, vol. 53, p. 1153-1169.*
NCBI Taxonomy search for *Streptomyces clavuligerus*.*
De Vries et al., Applied and Environmental Microbiology, 1997, vol. 63, No. 12, p. 4638-4644.*
El-batal, Food Research International, 2001, vol. 34, p. 715-720.*
Malherbe et al., Re/View in Environmental Science & Bio/Technology, 2002, vol. 1, p. 105-114.*
Mach et al., Applied and Environmental Microbiology, 1999, vol. 65, No. 5, p. 1858-1863.*
Chiou et al., Asian-australasian journal of animal science, 2002, vol. 15, No. 3, Abstract.*
Raimbault, M., EJB Electronic Journal of Biotechnology, 1998, vol. 1, No. 3, p. 174-188.*
Palit et al., Brazilian Archives of Biology and Technology, 2001, vol. 44, No. 1, p. 107-111.*
Pandey et al., Current Science, 1999, vol. 77, No. 1, p. 149-162, 22 pages in pdf.*
Viveros et al., J. Agric. Food Chem., 2000, vol. 48, p. 4009-4013.*
Pandey A., Biochemical Engineering Journal, 2003, vol. 13, p. 81-84.*
Asther et al., Process Biochemistry, 2002, vol. 38, p. 685-691.*
Dartora et al., Z. Naturforsch, 2002, vol. 57c, p. 666-670.*
Gutierrez-Correa, Marcel et al.: "Mixed culture solid substrate fermentation of *Trichoderma reesei* with *Aspergillus niger* on sugar cane bagasse" Bioresoejrc Technol; Bioresoijrce Technology, May 1999 Elsevier Sd Ltd, Exeter, Engl, vol. 68, No. 2, May 1999 (1999 pp. 173-178, XP001204371.

(Continued)

*Primary Examiner* — Kade Ariani
(74) *Attorney, Agent, or Firm* — Ballard Spahr LLP

(57) ABSTRACT

The present invention provides a method for directed selective solid-phase culturing of stable microbial mixed populations for the continuous preparation of defined enzyme and metabolite mixtures, enzyme and metabolite materials obtained by such method and suitable devices therefore.

23 Claims, 18 Drawing Sheets

(56) References Cited

OTHER PUBLICATIONS

Madamwar, D et al.: "Formation of Cellulases by CO—Culturing of *Irichoderma-reesei* and *Aspergillus-niger* on Cellulosic Waste," World Journal of Microbiology and Biotechnology, vol. 8, No. 2, 1992, pp. 183-186, XP009041572 ISSN: 0959-3993.

Castillo, Maria R, et al.: "Mixed culture solid substrate fermentation for cellulolytic enzyme production" Biotechnology Letters, vol. 16, No. 9, 1994, pp. 967-972, XP009041573 ISSN: 0141-5492.

Alam, Md. Zahangir, et al.: "Bioconversion of domestic wastewater sludge by immobilized mixed culture of *Penicillum corylophilum* WWZA1003 and *Aspergillus niger* SCahmAlO3," Artificial Cells Blood Substitutes and Immobilization Biotechnology, vol. 30, No. 4, Jul. 2002, pp. 307-318, XP008016282 ISSN: 1073-1199.

Patent Abstracts of Japan, vol. 2000, No. 25, Apr. 12, 2001 & JP 2001 231551 A (Kondo Takashi; Harada Chihiro; Hirano Minoru), Aug. 28, 2001—abstract; and & Database WPI Section Ch, Week 200170 Derwent Publications Ltd., London, GB; AN 2001-609958 XP002325971 & JP 2001 231551 A (Harada C) Aug. 28, 2001 abstract.

\* cited by examiner

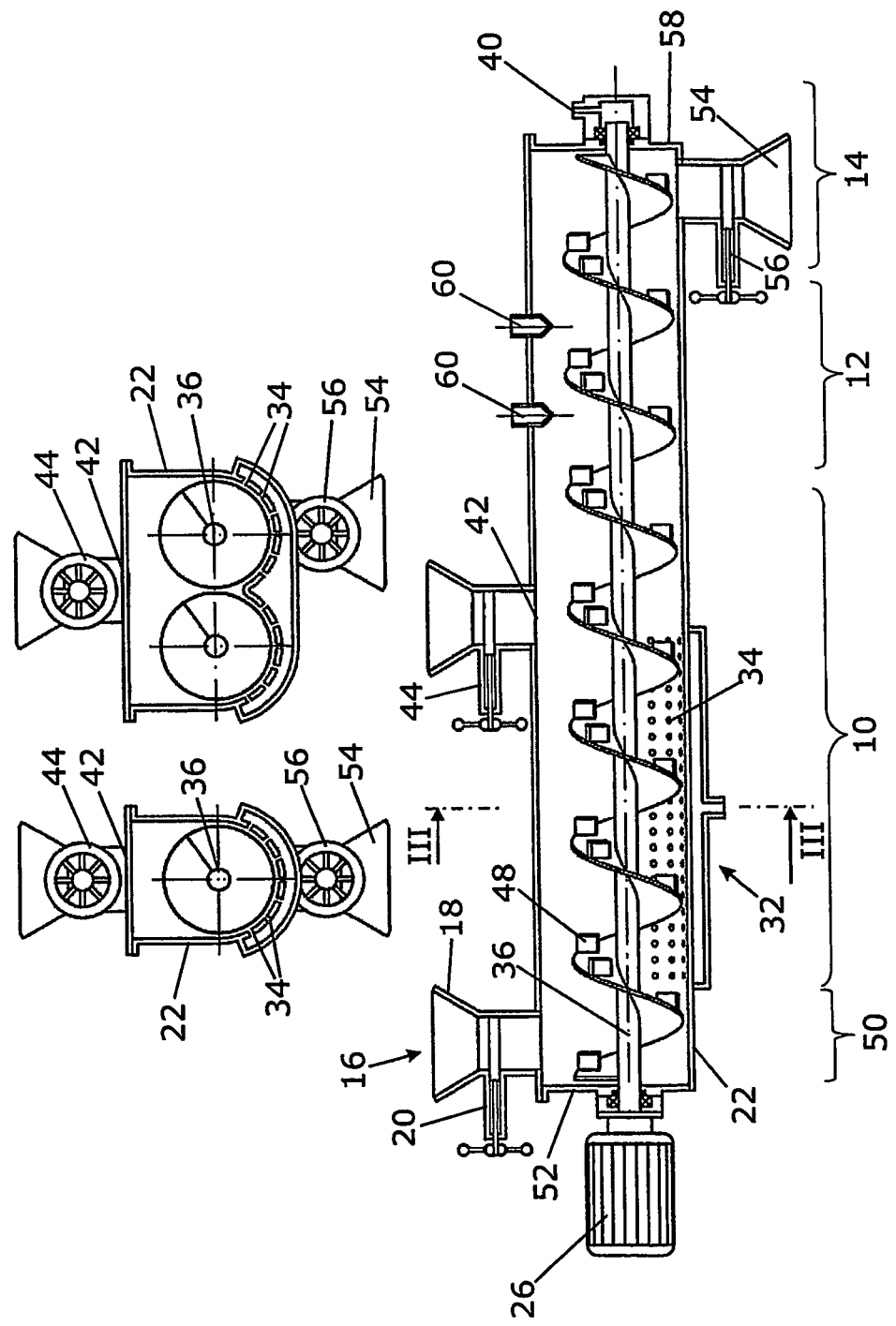

DIRECTED SELECTIVE SOLID-PHASE CULTURING OF STABLE MICROBIAL MIXED POPULATIONS FOR THE CONTINUOUS PREPARATION OF DEFINED ENZYME AND METABOLITE MIXTURES

The present invention provides a method for directed selective solid-phase culturing of stable microbial mixed populations for the continuous preparation of defined enzyme and metabolite mixtures, enzyme and metabolite materials obtained by such method and suitable devices therefore.

In particular the invention provides a novel culturing method, which is characterized in that a preculture of mixed organisms adapted to solid or liquid, optimally inductive substrates is preliminarily employed as an inoculating culture for producing a stable mixed culture of fungi, the actual main culture, which is continued by contacting it in a solid-phase bioreactor with one or more target substrates alone or in any possible combinations with other substrates or with these alone, and that the mixed culture is kept under an appropriate selection pressure by a suitable selection of the culturing parameters and by a specific induction by the target substrate(s) and/or inhibition with special inhibitors, and after a defined culturing time, a defined enzyme mixture and/or metabolite mixture optimized for the target substrate(s) is produced, which is employed for the saccharification of all kinds of natural polysaccharide substrates or for the degradation of vegetable, animal or microbial polymers.

BACKGROUND OF THE INVENTION

In the last decades, attempts have been increasingly made to treat biomass by enzymatic digestion (see, for example, DE-A-19845207). Thus, today, a number of approaches exist in which purified enzymes or enzyme mixtures or other enzyme-producing microbial pure or mixed cultures are employed for treating biological substrates. Examples include the treatment of wood chops in the course of biopulping, the treatment of annual plants for improving the properties as a fodder or of bagasse for preparing bioalcohol. However, all these processes still have a less than optimum course. The main reason thereof is that the enzyme mixtures, microorganism cultures or microorganism mixed cultures employed are not optimally adapted to the target substrates (e.g., the organisms and enzymes are not optimally adapted to and selected for cold to very cold locations), which results in very long treatment times of the chops, for example, in biopulping, with corresponding great space requirements for the stack areas.

Many biotechnological processes for the treatment of complex substrates (mostly plant material, but also animal waste from slaughterhouses etc.) often additionally require particular cofactors, e.g. specific tailor-made accompanying enzymes or mediators, which are in part still unknown, in addition to the known enzyme mixtures (hydrolases, oxidoreductases) for a possibly extensive degradation (mainly for oxidoreductases). This means that single enzymes or even additions of mixtures to the process are only conditionally successful because only a cooperation of enzyme mixtures previously adapted to and optimized for the target substrates together with these additional factors can show an optimum performance. However, to date, this has not been possible in an optimum way either.

From DE-A-3539875, for example, a method and a device for the continuous preparation of an enzyme mixture for the treatment of biomass in biogas plants have been known. However, a pure culture of *Aspergillus niger* is employed without induction of this culture by the plant substrates later used for the methanization. Therefore, it cannot be expected that the enzyme mixture formed thereby is optimally adapted to the biomass-utilizing process.

Defined enzyme mixtures and/or metabolite mixtures which are optimally adapted to a complex biological substrate can be produced only by exerting a selection pressure on the producing microorganism populations (mixed cultures) and/or their induction by the corresponding target substrates.

Now, it is generally known that the application of a selection pressure to mixed populations of microorganisms by adjusting defined environment parameters in the course of the culturing of these organisms usually leads to particular population spectra. However, these population spectra are non-directed and random.

It is also known that particular species of microorganisms can be enriched or contaminants suppressed by selecting the culture conditions.

It is also known that metabolite spectra which vary in time can occur during the course of such cultures as a function of the selection conditions chosen, but also as a function of the nature of the substrate and the availability of inducers (for non-constitutively formed proteins and metabolites). However, these metabolite spectra are also non-directed and random.

Methods of the type mentioned are employed, for example, on defined solid substrates (agar plates→mutagenesis treatments, genetic transformations etc.) and in the field of the submerged culture technique (in the form of chemostats or turbidostats also continuously). In the latter case, the cultures are mainly pure cultures for achieving specific metabolic performances.

Bioreactors for the continuous reaction of solid substrates are known from different fields of application (food technology, composting technology etc.). For example, the fermentation matter is conveyed through rolls in composting plants. However, such methods do not allow for a demanding regulation of the culturing parameters. For example, the use of one or more conveying screws in solid-phase bioreactors has been known from DE-A-10041977, DE-A-4308920 and DE-A-4208920. However, these bioreactors do not have a modular design and also fail to provide a possibility of a later addition of substrates and other substances, for example, for induction. Although the bioreactor mentioned in DE-A-100 29 668 is a segment screw conveyor, in contrast to the reactor according to the invention, it cannot utilize the time-dependence of the quantitative or qualitative production of the enzyme mixtures as a control variable for a feedback control of the running process itself, but also for the downstream target processes, i.e., it does not possess adjusting options and control of pH and moisture as a preferred property according to the invention, it cannot be optionally sterilized, and in particular, it also fails to possess a possibility for the metered addition of substrates, target substrates, inducers, inhibitors etc. according to the invention, and it fails to possess possibilities of inoculating and withdrawing growth-supporting enzyme-containing substrate during the initial growth process and the enzyme forming process.

DESCRIPTION OF THE INVENTION

A wide variety of technological processes are known in which enzymes have been employed in a less than optimum way or not at all, even though their use would provide a great economical and ecological benefit. These include, for example, methods comprising the change or conversion of complex biological solid substrates whose composition is very heterogeneous and which, above all, also contain hardly degradable substances, such as lignocellulose, and/or have outer boundary layers (e.g., lignified cell walls, cuticula etc) which represent barriers to enzymes and thus limit bioavailability. For an effective treatment of these substrates, enzyme mixtures especially optimized for these substrates would be necessary. To date, this has not been possible as a selective and directed preparation by corresponding fermentations.

A new continuous culturing method on the basis of a solid-phase growing technique by means of a special solid-phase bioreactor, a novel modular screw reactor, was found which is characterized in that a stable microbial culture, preferably a mixed culture of fungi, is provided by contacting it in the bioreactor with one or more target substrates alone or in any possible combinations with other substrates or with these alone, the term "target substrate(s)" intending to mean those which are employed in a subsequent process, and "substrates" meaning those which mainly serve for the optimization of the cell mass for an optimum quantitative enzyme production.

Moreover, it has been found that a general drawback—namely long growing times of the mixed cultures on the target substrates, target substrate/substrate mixtures or substrates, and the fact that optimum enzyme yields can be achieved only after extended culturing times—could surprisingly be overcome by modifying the above process in such a way that a preculture of mixed organisms adapted to solid or liquid substrates is preliminarily employed as an inoculating culture for producing a stable microbial culture, preferably a mixed culture of fungi as the actual main culture, which is continued by contacting it in a solid-phase bioreactor with one or more target substrates alone or in any possible combinations with other substrates (inducer substrates) or with these alone. The mixed cultures, which will produce a defined enzyme mixture and/or metabolite mixture optimized for the target substrate(s) after a defined culturing time (viz. under an appropriate selection pressure by a suitable selection of the culturing parameters and by a specific induction by the above mentioned target substrate(s) and/or inhibition with special inhibitors), are suitable for the subsequent process for the degradation of the target substrate(s) in a "step by step" or continuous manner.

This previous adaptation of the mixtures of, preferably, fungi on special inductive preculture media (solid/liquid) according to the above invention surprisingly not only entrains a substantial increase in enzyme yield in the main culture(s), but also substantially shortened growing times on the main culture media, which is also important to the subsequent cultures on the target substrates.

Moreover, it was found that enzymes produced in a solid state fermentation could be conserved by successive decrease of the water activity. Finally, it was found that the sequential cultivation of microorganism, in particular fungi in a solid state fermentation, could be controlled by the water activity.

The invention further provides a bioreactor for performing the described cultivating method according to the invention.

In particular, the present invention provides (1) a culture method for producing a defined enzyme mixture and/or metabolite mixture optimized for the fermentation of one or more target substrates by contacting an inoculating mixed culture of microorganisms in a solid-phase bioreactor with one or more target substrates, one or more inducer substrates or any combination of target and inducer substrates, and by keeping the mixed culture under an appropriate selection pressure by a suitable selection of the culturing parameters and by a specific induction by the target and/or inducer substrate and/or inhibition with appropriate inhibitors for a defined culturing time;

(2) an enzyme mixture and a metabolite mixture obtainable according to the method of (1) above;

(3) fermentation method for processing one or more target substrates which comprises fermenting the target substrates with an enzyme mixture and/or metabolite mixture obtainable by the method of (1) above;

(4) a method for the conservation of enzyme-mixtures produced in solid state fermentation which comprises decreasing the water activity of the substrates during the fermentation process, preferably by air flow through the substrate; and or by a final drying step, preferably in a fluidised bed or belt dryer;

(5) a method for the cultivation of microorganisms at equal growth rates by adjusting the water activity; and (6) a bioreactor, preferably a solid phase bioreactor for performing the method of (1) above.

The bioreactor comprises a fermentation module for the production of the method cultures under selection process. The fermentation module comprises a regulation means to adjust a fermentation environment. The regulation means may comprise aeration means and/or liquid feeding means to feed air and/or liquid to the fermentation area. These means are particularly nozzles. Furthermore, the bioreactor according to the invention comprises a feeding means being connected to the fermentation module to feed substrates to the fermentation area. Additionally, the bioreactor comprises an induction module for adding reagents such as agents for conferring selection pressure or inhibitors to the fermentation media being transported from the fermentation module to the induction module. Additionally, a harvesting module is connected to the induction module whereby the harvesting module comprises outlet means for the fermented substrate. To convey the media from the fermentation module through the induction module to the harvesting module a conveying means is provided. This conveying means is particularly located in a common housing whereby the fermentation module, the induction module and the harvesting module are located within this housing.

SHORT DESCRIPTION OF THE FIGURES

FIG. 2 shows a schematic side view of another embodiment of the bioreactor according to the invention.

FIG. 3 shows a schematic sectional view along the line III-III in FIG. 2.

FIG. 4 shows a schematic sectional view of another embodiment being comparable to the one shown in FIG. 3.

DETAILED DESCRIPTION OF THE INVENTION

Figure 1:
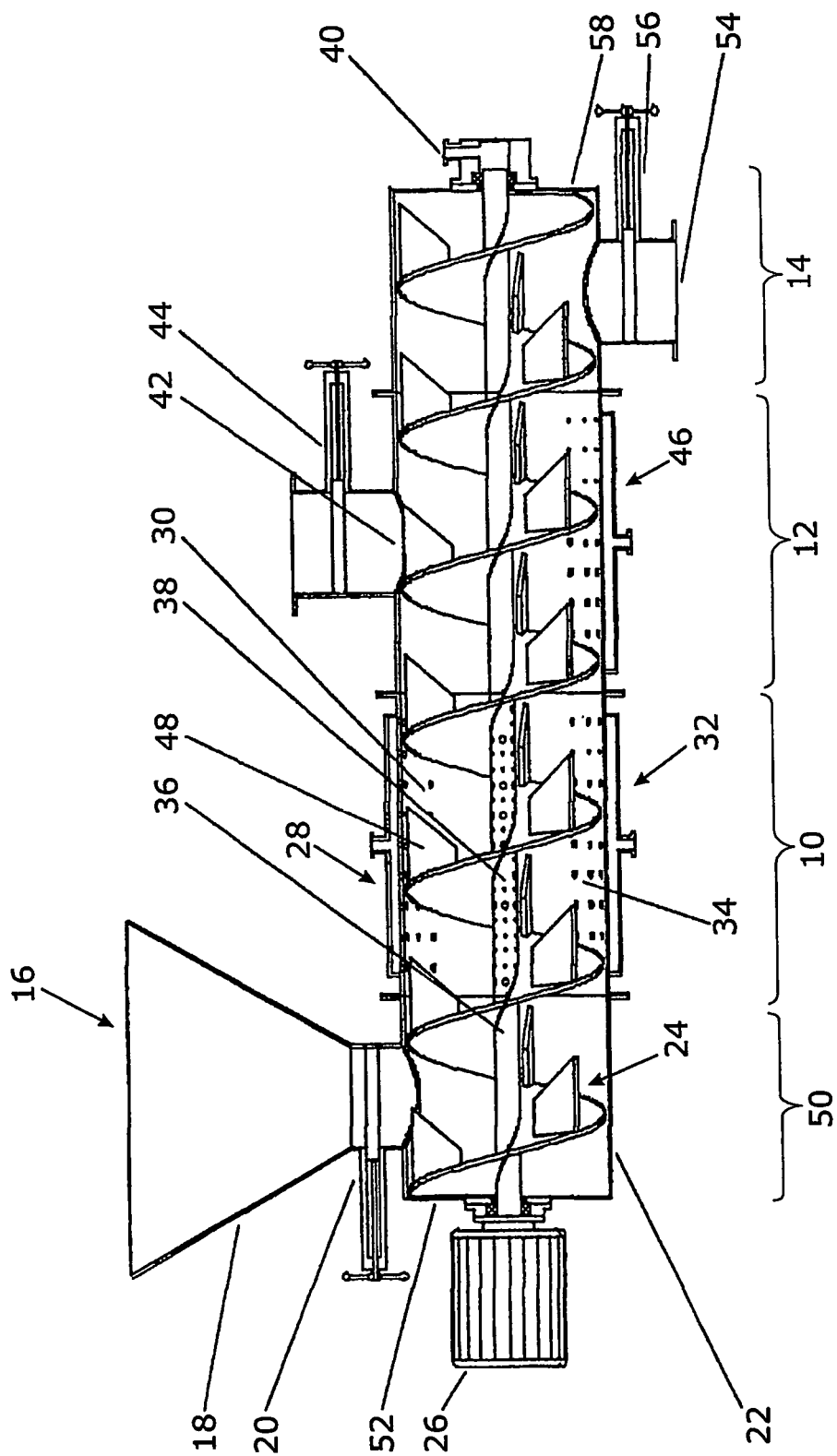
FIG. 1 shows a schematic side view of a preferred embodiment of the bioreactor according to the invention.

In the culture method of embodiment (1) of the invention a preculture of mixed organisms adapted to solid or liquid substrates is preliminarily employed as an inoculating culture for producing a stable microbial culture, preferably a mixed culture of fungi as the actual main culture. This method is continued by contacting it in a solid-phase bioreactor with one or more target substrates alone or in any possible combinations with other substrates or with these alone.

The term "target substrate(s)" according to the invention relates to those substrates which are intended to be employed in a subsequent fermentation process. Such target substrates include any plant- animal or microbial material which have to be modified or degraded "Inducer substrates" relate to substrates which mainly serve for the optimization of the cell mass for an optimum quantitative enzyme production. Suitable inducer substrates include plant- animal or microbial material The mixed cultures, which will produce a defined enzyme mixture and/or metabolite mixture optimized for the target substrate(s) are obtained after a defined culturing time under an appropriate selection pressure by a suitable selection of the culturing parameters and by a specific induction by the above mentioned target substrate(s) and/or inhibition with special inhibitors. Such mixed cultures are suitable to be employed in subsequent processes for the degradation of the target substrate(s) in a "step by step" or continuous manner.

The solid or liquid substrates for producing adapted precultures of mixed organisms as an inoculating culture for producing stable microbial cultures, preferably mixed cultures of fungi, may be, on the one hand, normal agar substrates which are inoculated with mixed cultures and which contain, as the corresponding inductive substrates, so-called "natural substrates", ground target substrates, target substrate/substrate mixtures or substrates, or polysaccharides (e.g., celluloses, hemicelluloses, pectins), proteins, lipids etc. or their mixtures as so-called "synthetic substrates", and also mixtures of "natural substrates" and "synthetic substrates". The method of embodiment (1) of the invention is preferably performed under aerobic conditions.

On the other hand, they may also be any liquid cultures, such as shaking flasks or fermenter cultures, in which chemostat or turbidostat cultures may also be employed for fermenter cultures for the selection of high-performance strains, or "solid state" (SSF) cultures which work with carriers as an inert growing medium, e.g., in column reactors, and which are bathed with the corresponding substrate or mixtures of substrates.

Further, adapted precultures of mixed organisms as an inoculating culture for producing stable microbial cultures, preferably mixed cultures of fungi, may also be cultures which have run through an inductive preculture and one or more main cultures operated under a selection pressure. The thus obtained highly selective inoculating cultures can be directly employed or preserved by methods such as freezing, lyophilization and similar techniques (according to the prior art) and then employed when used.

The corresponding selection pressure provided by varying the culturing parameters is adjusted and maintained by suitably selecting the moisture content (water activity), pH value, temperature, oxygen availability, redox potential and nutrient composition etc., as well as by specific induction by the above mentioned target substrate(s) and/or inhibition with special inhibitors.

Special inhibitors include those described, for example, in R. Vogel, Natürliche Enzyminhibitoren, Georg Thieme Verlag, 1984, and in H. Zollner, Handbook of Enzyme Inhibitors, VCH, 1989, e.g. protease inhibitors derived from plants Controlling the water activity is the most preferred mode for building up selection pressure. A water activity between 0.85 and 0.99 is particularly preferred.

A further important feature of the method of embodiment (1) of the invention is the fact that white rot fungi are employed as fungal cultures for producing adapted precultures of mixed organisms as an inoculating culture for producing stable microbial main cultures, which white rot fungi mainly provide manganese peroxidase (MnP) and laccase for downstream microbiological processes, such as degradation reactions or hydrolysis reactions or microbial conversions coupled to these, such as methane fermentations, alcoholic fermentations etc. The $H_2O_2$ required for the activity of MnP is either supplied continuously in small dosages or generated in situ by means of enzymes, such as glucose oxidases I and II (GOD I and II), glyoxal oxidase, methanol oxidase, galactose oxidase, cellobiose quinone oxidoreductase (CBQ) or cellobiose dehydrogenase (CDH), etc.

It is known that these enzymes are capable of demethylating lignin to a substantial extent with or without simultaneously degrading the lignin.

The methyl alcohol $CH_3OH$ formed is partly oxidized to $CO_2$ and simultaneously reduced by the hydrogen formed to form methane ($CH_4$) according to the following summation equation:

$$CH_3OH + H_2O \rightarrow CO_2 + 6H$$

$$3CH_3OH + 6H \rightarrow 3CH_4 + 3H_2O$$

$$4CH_3OH \rightarrow 3CH_4 + CO_2 + 2H_2O$$

Since the lignin content is relatively high and may be up to 20% of dry matter in many raw and waste materials, especially agricultural ones, considerable methane resources can be exploited. As an additional effect, the content of available residual oxygen could be further minimized by the action of the laccases and also of the $H_2O_2$-producing enzyme systems, which should have a beneficial effect on the course of the fermentation.

In fermentations effected downstream of the hydrolysis or the degradation of raw and waste materials, such as methane fermentations, alcoholic fermentations etc., or generally, the reduction of hardly exploitable waste materials by the degradation of lignin substances by laccase or $MnP/Mn^{3+}/H_2O_2$ systems could also provide a significant benefit.

A further important feature of the method according to embodiment (1) of the invention is the fact that after the optimum inoculation of the main cultures according to the invention, the continuously produced enzyme/substrate/fungus mixtures are either employed as such in subsequent processes, or a separation of the substrate/fungus mixture is effected to obtain a liquid enzyme cocktail.

Further, it is possible to subject the thus obtained liquid enzyme mixtures to further downstream processing (purification by ultrafiltrations, chromatographic methods etc.).

A further important feature of the method of embodiments (1) and (3) of the invention is the fact that after the optimum inoculation of the main cultures according to the invention, the continuously produced enzyme/substrate/fungus mixtures are substituted by enzymes prepared by other methods (including commercially available ones) in a way as to add deficient important activities for the degradation or modification of the target substrates to the enzyme spectrum according to the invention.

Another important feature of the invention with the optimum inoculation according to the invention is the fact that the natural contamination population of particular target substrates/substrates is utilized for selecting desired germs having desired properties therefrom. The addition of such germs is effected at the beginning of the culturing, i.e., also already with the inoculation cultures, or additionally during the growth. Pure cultures of the organisms which naturally occur on these target substrates/substrates and/or have been grown therefrom after isolation and determination or those which are derived from collections or other strains or organisms (e.g., high-performance strains) which have a suitable enzyme spectrum may also be added directly to the inoculation cultures or additionally during the main culture.

A further important feature of the invention is the fact that after the optimum inoculation according to the invention, the main culture in the method according to the invention may consist of one to several process steps. These process steps may generally proceed simultaneously, i.e., simultaneously employed target substrates and/or substrates (singular or plural) are used, and additional inducers and/or inhibitors may be added simultaneously or sequentially during the course of the culture. However, the process steps may also be performed successively in time by the sequential use of singular or plural target substrates and/or substrates.

This is enabled, inter alia, by the continuous process operation and modular design of the bioreactor described in embodiment (6) and that of DE 10328552.0, which is preferred for the present method according to the invention and which, due to its design, enables an extra substrate addition, addition of other inducers, inhibitors, addition of microorganism cultures, change of the selection pressure etc. during the course of the culture.

The method described according to the invention with the optimum inoculation according to the invention can generally be performed with all similar "solid state" reactors which can utilize the time-dependence of the quantitative or qualitative production of the enzyme mixtures as a control variable for a feedback control of the running process itself, but also for a feedback control of the downstream target processes.

For cultures with several process steps (e.g., two-step), the optimum inoculation according to the invention using preinduced precultures (depending on the target process), wherein these precultures may consist of either a) organisms of the natural growth on the substrates to be inoculated and/or b) organisms which may consist of pure cultures (also high-performance strains or also strains from collections) or of mixtures of a) and b), in the first process phase is followed by producing a mixed main culture by selecting suitable substrates and/or target substrates, by adjusting further selective conditions by means of suitable selective adjustment of the water activity, pH value, redox potential, temperature, availability of oxygen, availability of inducers etc. The object of this first phase of the process is to provide a pool (qualitative and quantitative) of microbial populations and enzyme spectra which is suitable for the second process phase. In the second step of the process, the mixed culture is converted in a directed manner to a stable and optimally adapted mixed culture (fine tuning) by adding a further substrate and/or target substrate or several substrates at the same time and by adjusting selective conditions, optionally different from those in the first step, i.e. by suitably selecting the water activity, pH value, redox potential, temperature, availability of oxygen, availability of inducers etc., which mixed culture produces, after a defined culturing period, a similarly defined spectrum of enzymes and/or metabolites which is optimally adapted to the target substrates used for induction.

Due to the operation of the inoculation culture according to the invention which is optimized by selection pressure and induction, a significantly (qualitatively and quantitatively) improved enzyme yield and improved enzyme spectrum can be achieved with significantly reduced time requirements of culture adjustment and of the total culturing time.

A further important feature of the method of embodiment (1) of the invention is the fact that after the optimum inoculation according to the invention and the selective process operation according to the invention and before downstream processes, such as special fermentations, e.g., methane fermentation etc., the mixtures of microorganisms preinduced according to the invention are not only directly (e.g., by a screw reactor) supplied to the substrates to be hydrolyzed and simultaneously fermented (e.g., methane fermentations), but are first passed into a prehydrolysis container to initiate a preliminary saccharification or, in the optimum case, a complete hydrolysis of the polysaccharides and other polymers, such as proteins and fats. The corresponding hydrolyzates are then passed to the actual fermentation. This has the advantage of a better dosability of the required fermentable sugars with a correspondingly higher process security.

A further important feature of the method of embodiment (1) of the invention is the fact that after the optimum inoculation according to the invention and the selective process operation according to the invention and before downstream processes, the preinduced mixture of microorganisms is transferred to another solid state process operation in which the whole substrate (which is to be fermented later, for example) is selectively utilized for producing enzymes and at least partially hydrolyzed. Preferably, mixtures of organisms, e.g., mixtures of white rot fungi, which metabolize only low amounts of sugar at high enzyme forming rates are to be employed.

It is further preferred to additionally incorporate the mixed populations, which were produced according to the invention in a side stream (e.g., screw reactor) (according to the method according of the invention with optimum inoculation according to the invention and selective process operation according to the invention), into the subsequent fermentations (e.g., methane fermentation) by means of mixed populations of other microorganisms.

A further important feature of the method of embodiment (1) of the invention is the fact that after the optimum inoculation according to the invention and the selective process operation according to the invention, the preinduced mixture of microorganisms (bacteria and fungi) is transferred to another solid state process operation in which the whole substrate is selectively utilized for producing enzymes and at least partially hydrolyzed or converted, e.g., for composting purposes. Another preferred application is the degradation of xenobiotics, in particular.

Moreover, the method according to embodiment (3) of the invention can be applied to all technological processes in which biological substrates are changed or converted, and a treatment of these substrates by enzymes is either included in the processes themselves or can be utilized as a preliminary or additional treatment. This applies, in particular, to processes from:

1) the wood-processing industry, such as paper and pulp industries;
2) the textile industry;
3) the leather industry;
4) the animal-processing industry;
5) the detergent industry;
6) the fodder industry;
7) the food industry;
8) the waste water, exhaust air and soil purification;
9) the processing of residual materials; and
10) to processes employed for the processing of raw materials from naturally renewable resources.

Beyond the possible applications mentioned above, it could be surprisingly found that the method according to the invention can serve for further significantly increasing the availability of or digesting substances whose yield cannot be further optimized (quantitatively or qualitatively) by normal chemical processes.

Preferably, these are hardly accessible residual materials, such as residual sugars (polymers, oligomers etc.), proteins, fats and other polymers, or generally biologically extractable, degradable or modifiable substances, which includes a considerable increase of the creation of value of the whole, mostly upstream, process, which is usually a chemical process.

Such processes optimized according to the invention include, for example, the post-extractions of chemically pre-extracted materials, such as sugar beet chips, sugar cane, cereals and other vegetable and animal raw or waste materials, performed by means of the system according to the invention.

The main object of employing the method according to the invention, for example, in the treatment of sugar beets, is the increase of the yield of recoverable sugars by further enzymatic extraction and/or enzymatic hydrolysis from the residuals of chemical extraction, such as exhausted chips, i.e., especially the release and optionally hydrolysis of sugar contents remaining in the tissue parts of the chips (difficult to recover chemically). These, in this case, sugars can then be purified, separated, refined, converted to other materials or converted to other energy carriers in further processes.

Further, the method according to the invention (generally or for this special application case) may also be a part of a particular treatment line, i.e., a chemical and/or enzymatic and/or microbial treatment, for example, may be employed upstream, and a further chemical and/or enzymatic and/or microbial process may be employed downstream, the term "microbial processes" meaning those which work with growing microorganisms (mainly bacteria and/or fungi), such as fermentations (alcoholic fermentations, methane fermentations) or generally transformation of matter processes.

The enzyme mixture of embodiment (2) of the invention is applicable in textile industry, wood-processing industry (paper, pulp and wood board industries, biopulping), detergent industry, leather industry, animal-processing industry, fodder industry, food industry. In these applications, the enzyme mixtures according to the invention, prepared by optimum inoculation according to the invention and selective process operation according to the invention, are to be employed preferably for the degradation, conversion or modification of the corresponding substrates, i.e., enzyme cocktails are to be provided which, in contrast to commercially available enzymes, for example, possibly possess all the enzymes and, if required, cofactors necessary for the degradation, conversion or modification of the respective substrates, to be able to perform the substrate changes mentioned in an optimum way.

Moreover, the enzyme mixture is applicable in processes concerning the treatment of waste water, exhaust air and soil purification, processing of residual materials and processes employed for the processing of raw materials from naturally renewable resources. In these applications, the enzyme mixtures prepared according to the invention, prepared by optimum inoculation according to the invention and selective process operation according to the invention, are also preferably to be employed for the degradation, conversion or modification of the corresponding substrates. In addition, in wastewater purification, the waste waters to be purified are to be employed as inducer substrates, which may be effected anywhere in the induction cascade, to obtain the optimally adapted mixtures of organisms and enzymes. In the exhaust air purification, the relevant polluting gases are to be passed to oxygen aeration as an inductive partial stream, and in soil purification, the loaded soils are also to serve as an induction substrate.

In the processing of raw materials from naturally renewable resources, the enzyme mixtures prepared according to the invention, prepared by optimum inoculation according to the invention and selective process operation according to the invention, as mentioned above, are to be prepared, for example, as a hydrolysis catalyst, preferably before processes such as biogas production, bioethanol production, composting (production step) and brought to effect either before (hydrolysis step, e.g., bioethanol production, biogas production, composting) and/or during such process steps.

In addition to the preferred bioreactor described in DE 10328552.0 and those mentioned in embodiment (6) of the invention which are particularly suitable for the continuous performance of the reported method according to the invention, in principle, other solid-state bioreactors for the solid phase culturing of microorganisms are to be employed, such as those mentioned in our own applications WO 01/19954, WO 02/100999 A2, PCT/EP 03/01663, or generally screw reactors, drum reactors, tower reactors, trickling film reactors, horizontal mixers, vertical mixers etc., optionally modified or in the form of a cascade. Particularly preferred are reactors based on the principle of constant conveyors, flexible screws, endless screws, which function according to the principle of screw conveying, pressure screw conveying, screw conveying according to the principle of a solid-state air-lift reactor etc., or conveying belt transport, individually or preferably in a cascade form. The described method according to the invention with the optimum inoculation according to the invention can be generally performed with all solid-state reactors which can utilize the time-dependence of the quantitative or qualitative production of the enzyme mixtures as a control variable for a feedback control of the running process itself, but also for the downstream target processes, i.e., which, as preferred properties according to the invention, may be generally sterilizable, should be aerated, dispose of adjusting facilities (adjustment, feed-back control) for pH, moisture and temperature and, in particular, should have the possibility of metering substrates, target substrates, inducers, inhibitors etc. according to the invention, and should possess possibilities of inoculating and growth-supporting enzyme-containing substrate.

The cascade form is particularly preferred for utilizing the time-dependence of the production of the enzyme mixtures for their optimization in view of the degradation of the target substrate(s) simultaneously and sequentially, i.e., it becomes possible to supply one or more processes downstream of the enzyme forming process with correspondingly optimized enzyme cocktails simultaneously or sequentially. Also, it becomes possible to balance time differences during the production by using the cascade as a "closed loop" and connecting several cascades in parallel.

In addition to all kinds of continuous and fed-batch processes, batch processes in the mentioned reactors or processes are also preferred, either per se or in processes in which batch processes are employed alternately with continuous processes and/or fed-batch processes.

Moreover, the present invention provides a process for conservation of enzyme-mixtures produced in the solid state fermentation (SSF) by successive decrease of the water activity. For microbial growth water is essential. Microorganisms have different demands for water. While bacteria and yeasts prefer water activities near 1 (with the exception of halophilic species), filamentous fungi tolerate lower water activities. In solid state fermentation (SSF) processes the different demand for water can be used for semisterile processing. This offers the possibility to cultivate fungi on solid substrates without sterilisation of the substrate. During microbial growth on solid substrates the water activity changes because of different chemical and physical changes caused by microbial degradation of the substrates and because of metabolic water produced by the microorganisms. In semi-sterile processes the excess of water enables unwanted bacteria to grow. Since the substrates used in SSF are inhomogeneous, water activity is, in contrast to submerged fermentation processes, difficult to control. The increase of water activity occurs in SSF predominantly at the end of fermentation thus leading to water activities near one so that unwanted bacteria, producing proteases can grow and degrade the extracellular enzymes produced by the fungi.

During growth on solid substrates fungi secretes enzymes in high concentration. During the on-side production of enzymes in SSF the suitability for storage is not an important factor, since the production of enzymes is directly coupled to the consuming step. A conservation of the enzyme mixture is required when the product should be stored or transported. It is possible to conserve the produced material by freezing or lyophilisation, but on industrial scale this is connected with high costs which could make the process noneconomical.

Drying of the fermentation product is a relative slow process, since, in contrast to submerged fermentation spray drying is not possible. A fast drying with hot air leads to a significant loss of enzyme activity. A slow drying of the moist material by 20° C. air is negative, because proteases may hydrolyse the wanted enzymes.

Surprisingly it could be found that a new strategy to dry the enzyme containing material can be used to conserve the enzymes. In this process the water activity is decreased in an controlled way at the end of fermentation, starting from 0.98 to 0.96, to 0.94 in intervals between 1 and 6 hours. This treatment leads to a slow reduction of the fungal metabolism. Hydrolytic extracellular enzymes like proteases compete for water with the water holding capacity of the substrate and the living cells. The enzyme activities in the medium are surprisingly not affected. After the slow decrease of the water activity to 0.94 the fermentation product can be dried until the weight is constant in e.g. a fluidised bed air dryer. Enzyme-mixtures treated in this way can be stored without activity-loss for more than 6-8 weeks.

A further important feature of the method of embodiment (1) is the leaching of the produced enzyme containing solid (enzyme mixture) by moving or stirring it with water, buffer, detergent/water or detergent/buffer solutions [1 to 10 or 1 to 20 by weight (enzyme containing solid to solution)] for 30 min to 2 hours. The obtained enzyme slurry is filtered and the filtrate is further used as a solvent for additional leaching cycles (up to 10 times). A highly concentrated enzyme slurry is received which can easily be dried by the mentioned fluidized bed air dryer or other state-of-the-art methods.

The invention moreover provides a process for sequential cultivation of fungi in SSF by selective conditions created by a controlled water activity. In contrast to bacteria phylogenies of higher fungi (Ascomycetes and *Basidiomycetes*) took place on moist substrates and not in aqueous suspensions. Hence fungi are better adapted to water activities below 1 than are bacteria or yeasts. This fact can be used in SSF to fermentate substrates under semisterile conditions by avoiding a free macroscopic visible water phase. Also fungi are adapted in different ways to water activity and grow at different water activities with different grow rates.

It is possible to cultivate two fungi with the same growth rate by setting a compromise between the optimal water activities. The cultivation of more than two fungi with the same growth rates is difficult.

In the new continuous process it is possible to cultivate two fungi at the same water activity, but the water activity differs in different zones of the process. For example in zone 1 of the bioreactor a water activity of 0.99 for the growth of *Aspergillus niger* and *Aspergillus oryzae*, in zone 2 a water activity of 0.96 for the growth of *Neurospora crassa* and *Neurospora intermedia* and in zone 3 a water activity of 0.92 for the growth of *Penicillium chrysogenum* and *Penicillium roquefortii*. During this process the enzymes are produced by the preferred pair of fungi.

Preferably this process can also be regulated by discontinuously increasing the water activity. In this case the water activity is increased by addition of water which contains the appropriate spores.

Preferably this process can be used in the described continuous bioreactors mentioned in this application but also in drum-type SSF-reactors or other types which allow a forced aeration and have the possibility to trickle water onto the substrate under controlled conditions, to modify the growth conditions during fermentation.

For the hydrolysis of polymers in solid bed processes, which are percolated with fluids like in some bigas, bioethanol, biopulping or silage processes it is preferred to leach the enzymes produced in the claimed fermentation process in water. The produced enzyme mixture is solved in a 10 to 20 times higher volume of water and stirred for 1 to 2 hours.

The design and function and the corresponding operation of the preferred screw reactor and of the screw reactor cascade is described in detail in DE 10328552.0, the reactor is described in FIG. 1.

DETAILED DESCRIPTION OF THE FIGURES

The bioreactor according to of embodiment (6) of the invention is shown in the FIGS. 1 to 11.

With in the following description of various embodiments of the invention the similar parts are named by the same reference signs.

A first embodiment of the bioreactor (FIG. 1) comprises a fermentation module or a fermentation area 10. In addition to the fermentation module 10 the bioreactor comprises an induction module 12 and in connection to the induction module 12 a harvesting module 14 is provided. The fermentation module 10 is connected to a feeding means 16 via the driving module 50. The feeding means 16 comprises a hopper 18 and a closure means 20 so that substrate can be fed through the feeding means 16 to a particularly tuber housing 22.

The tuber housing 22 consists of the fermentation module 10, the induction module 12 and the harvesting module 14. Additionally, within the housing 22 a conveying means 24 being a conveying screw in the shown embodiment is located. The conveying means 24 conveys the media within the common housing 22 from the feeding means 16 via the driving module 50 to a fermentation module 10 through the induction module 12 to the harvesting module 14. To rotate the conveying screw 24 the conveying screw 24 is connected to a motor 26.

In the shown embodiment the fermentation module 10 comprises different kinds of regulation means. The regulation means include a liquid feeding means 28 being connective to an upper part of the tube housing 22. The liquid feeding means 28 comprises spraying nozzles 30 through which a liquid can be sprayed within the fermentation area 10. On the opposite side of the liquid feeding means 28 an aeration means 32 is located on the housing 22 whereby the aeration means 32 comprises aeration nozzles 34. An additional aeration and a liquid feeding means is part of a hollow shaft 36 of the conveying means 24. The hollow shaft 36 comprises within the fermentation module 10 nozzle orifices 38 through which liquid and/or air can be injected into the fermentation area 10. To do so the hollow shaft 36 may be connected via an inlet opening 40 with an liquid air supplying means.

The induction module 12 comprises a opening 42 to add targets, e.g. for conferring selection pressure to the media conveyed by the convey means 22 from the fermentation module to the induction module 12. The opening 42 is provided with a closure 44 whereby the opening 42 is located on the upper sidewall of the housing 22. On the opposite side of the housing 22 an aeration means 46 is located. In addition to that a liquid feeding means can be located within the induction module 12.

The bioreactor according to the embodiment shown in FIG. 1 consists of any number of modules desired, a total of 4 types of modules being provided. All modules consist particularly of a stainless steel tube in which a conveying screw 24 with the hollow shaft 36 is supported to rotate. The conveying screw 24 is provided with blades 48 for the verticals mixing of the fermentation matter. The individual modules and also the conveying screw 24 can be attached to each other through a suitable connection system. In the assembled state, the individual screw elements are commonly driven by a motor 26.

The fermentation module 10 has nozzle orifices 38 on the hollow shaft 36 of the conveying screw 24 through which the fermentation matter can be aerated. Further aeration nozzles 34 are distributed in the lower half of the tube wall. In the upper half of the tube wall, spraying nozzles 30 for the addition of liquid media are provided. The so-called induction module 12, which can be used for the addition of the materials in the method according to the invention, has an opening 42 with a closure means 44 for the addition of solid materials on the upper side of the tube wall. The driving module 50 has no nuzzles. Further, one of the two sides of the tube is closed by a sidewall 52. The driving motor and the bearing in the driving module 50 for the shaft are attached at the closed side wall 52.

On the upper side of the tube wall, a hopper 18 with a closure means 20 for the addition of solid materials and optionally for inoculate is provided. The harvesting module 14 has no nuzzles either. Instead, an opening 54 with a closure means 56 for removing the fermentation matter is attached there on the lower side of the tube wall. The second side of the tube is closed by a sidewall 58. The counter bearing for the hollow shaft is attached there. The bearing has a connection to the aeration 40.

The bioreactor shown in FIG. 2 is similar to the one shown in FIG. 1 whereby the aeration means 32 may also be used as liquid feeding means so that the liquid feeding means (FIG. 1) is not necessary. Additionally, within the induction module 12 no aeration- and/or liquid feeding means 46 is arranged. Instead of the opening 42 (FIG. 1) to add solid materials on the upper side of the tube, two openings 60 having a small diameter are provided.

As shown in FIG. 4, it is possible to arrange two conveying screws 36 next to each other increasing the mixing quality of the material within the housing 22.

Figure 5:
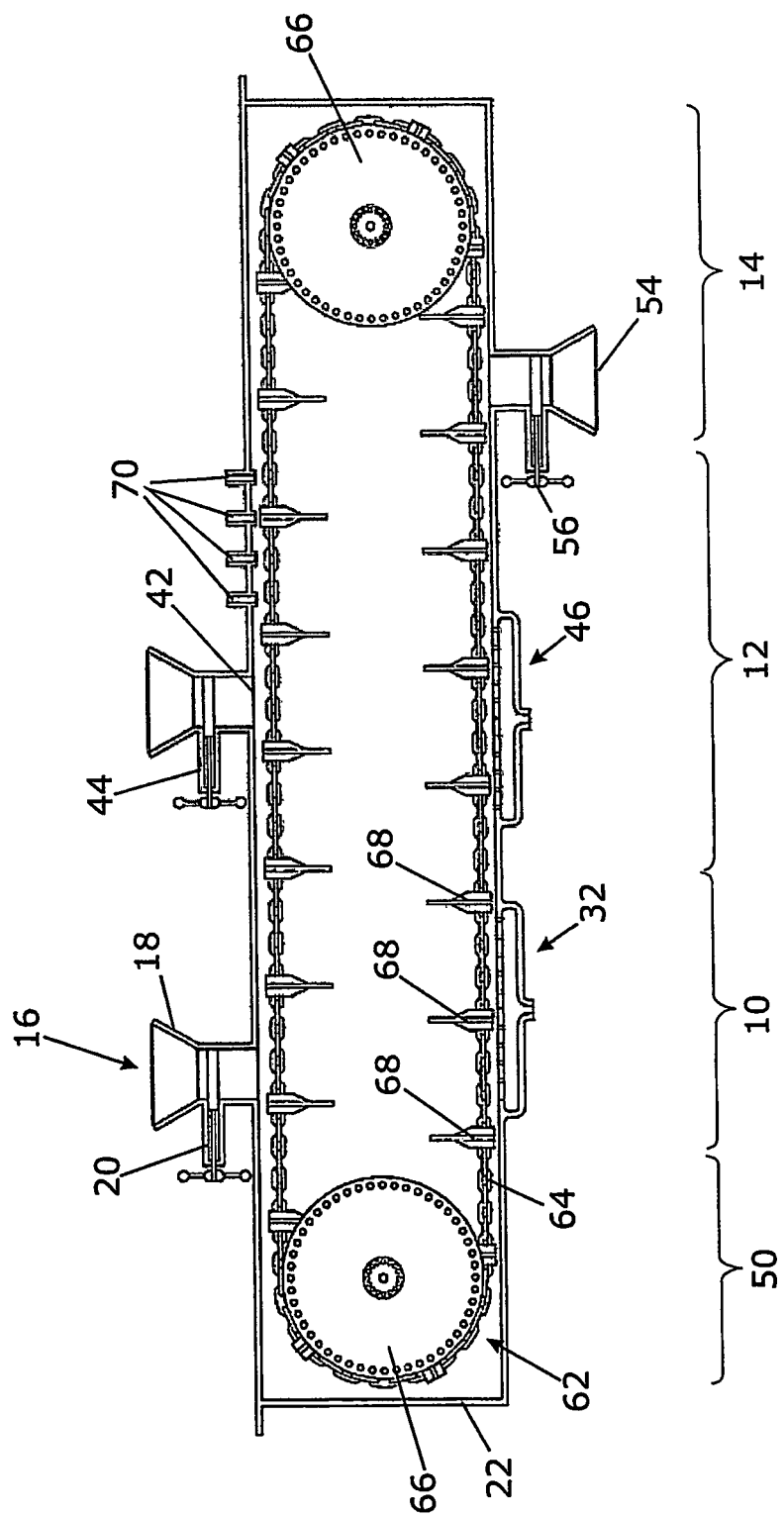
FIGS. 5-11 show schematic side views of different embodiments of the invention.

In view of the embodiment shown in FIG. 5, a chain conveyer 62 is used instead of a conveying screw 24. The chain conveyer 62 comprises a closed chain 64 being transported by two chain wheels 66 whereby one of these chain wheels is connected to a motor which is not shown. Blades 68 are connected to the chain in equal distances. In view of the induction module 12 an opening 42 is provided to add solid material. In addition to the opening 42 openings 70 are provided to add liquid material.

Figure 6:
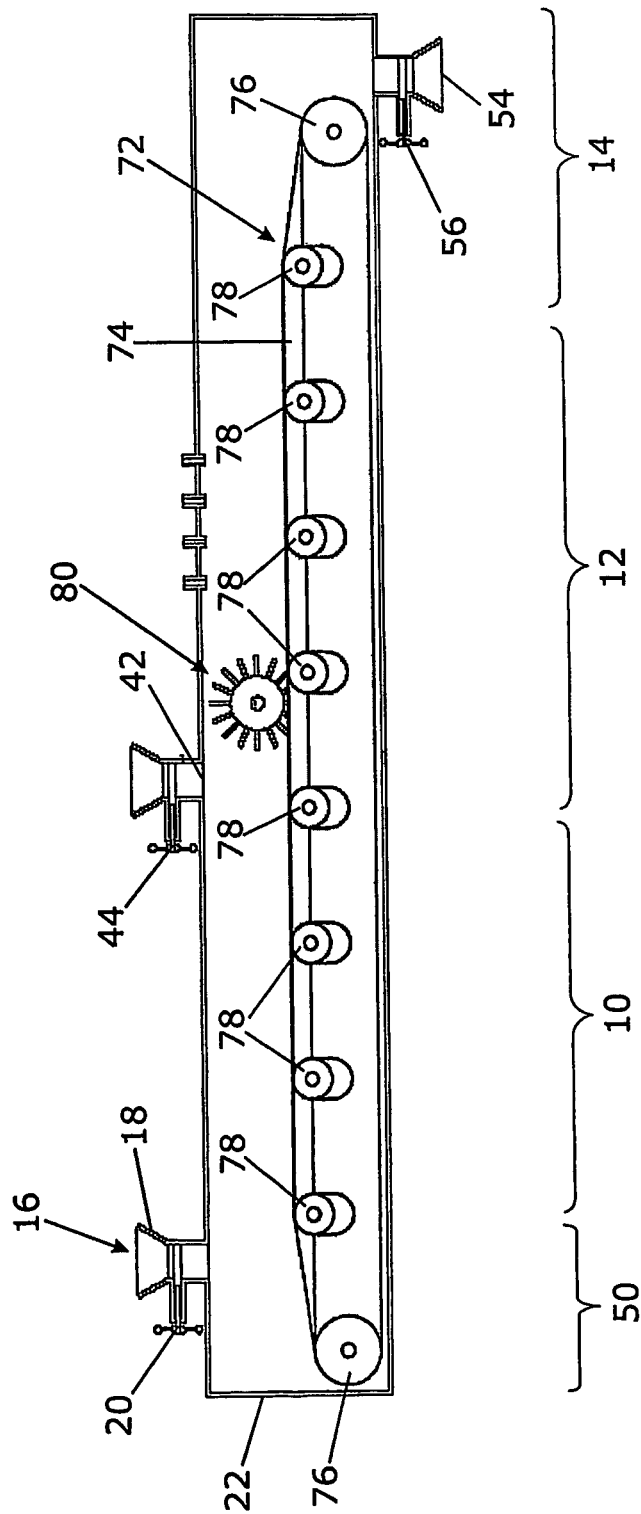

The embodiment shown in FIG. 6 has a belt conveyer 72 whereby the belt 74 is connected to two wheels 76. One of the wheels 76 is connected to the driving motor. In addition to an upper part of a belt conveyer, the belt 72 is supported by supporting roles 78. In the middle of the housing, within the induction module 12, mixing means 80 being driven by a motor are provided.

Figure 7:
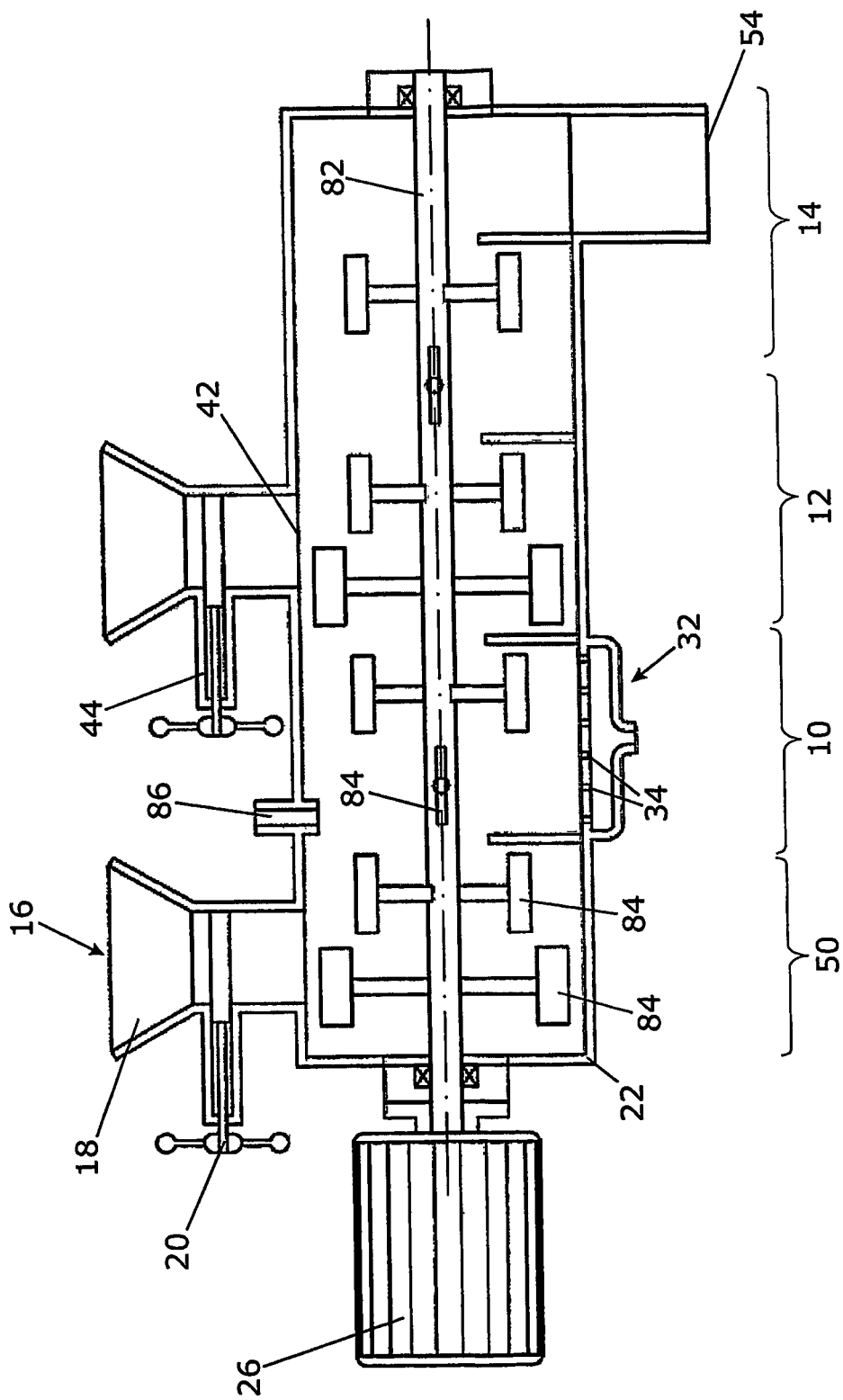

The embodiment shown in FIG. 7 has a axis 82. With the axis several mixing elements 84 having the hammer-like shape are connected. The mixing elements 84 are shifted by an angle so that the heads of the mixing elements 84 appear to be located in different distances to the axis 82 in the figure.

Figure 8:
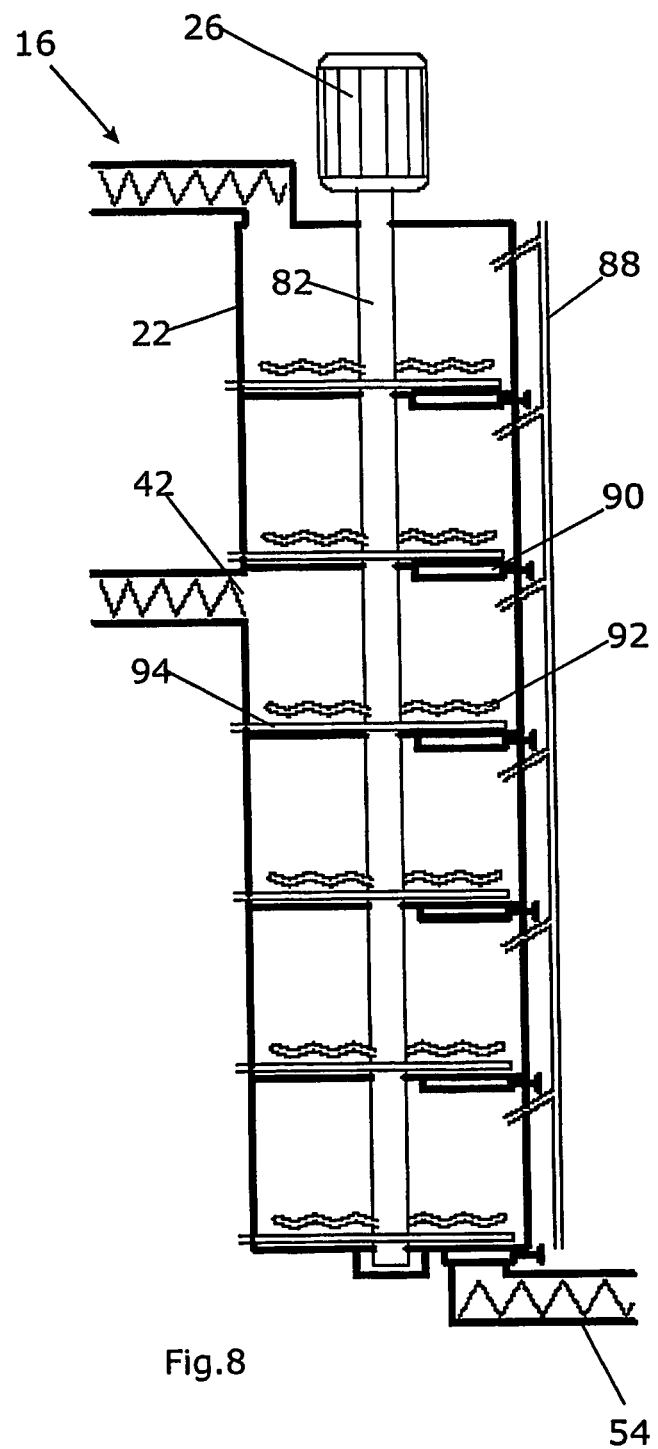

In view of FIG. 8 the material is transported periodically from top to bottom within the house 22. The material enters the bioreactor through the port 16, containing a conveying screw and leaves the bioreactor through a similar port 54. Addition of target substrate is performed through port 42. The material resists on floors 94 which contain which are equipped with a means for aeration. Water can be added to the material on the floors through nozzles connected to a water pipe 88. The material can be mixed during the resistive phase using mixing rods 92, which are attached to the central shaft 82. This shaft 82 rotates due to the action of a motor unit 26. To transport the material downwards from floor to floor leafs 90 closing a hole in each floor are periodically opened. The material trickles through the hole onto the next floor.

Figure 9:
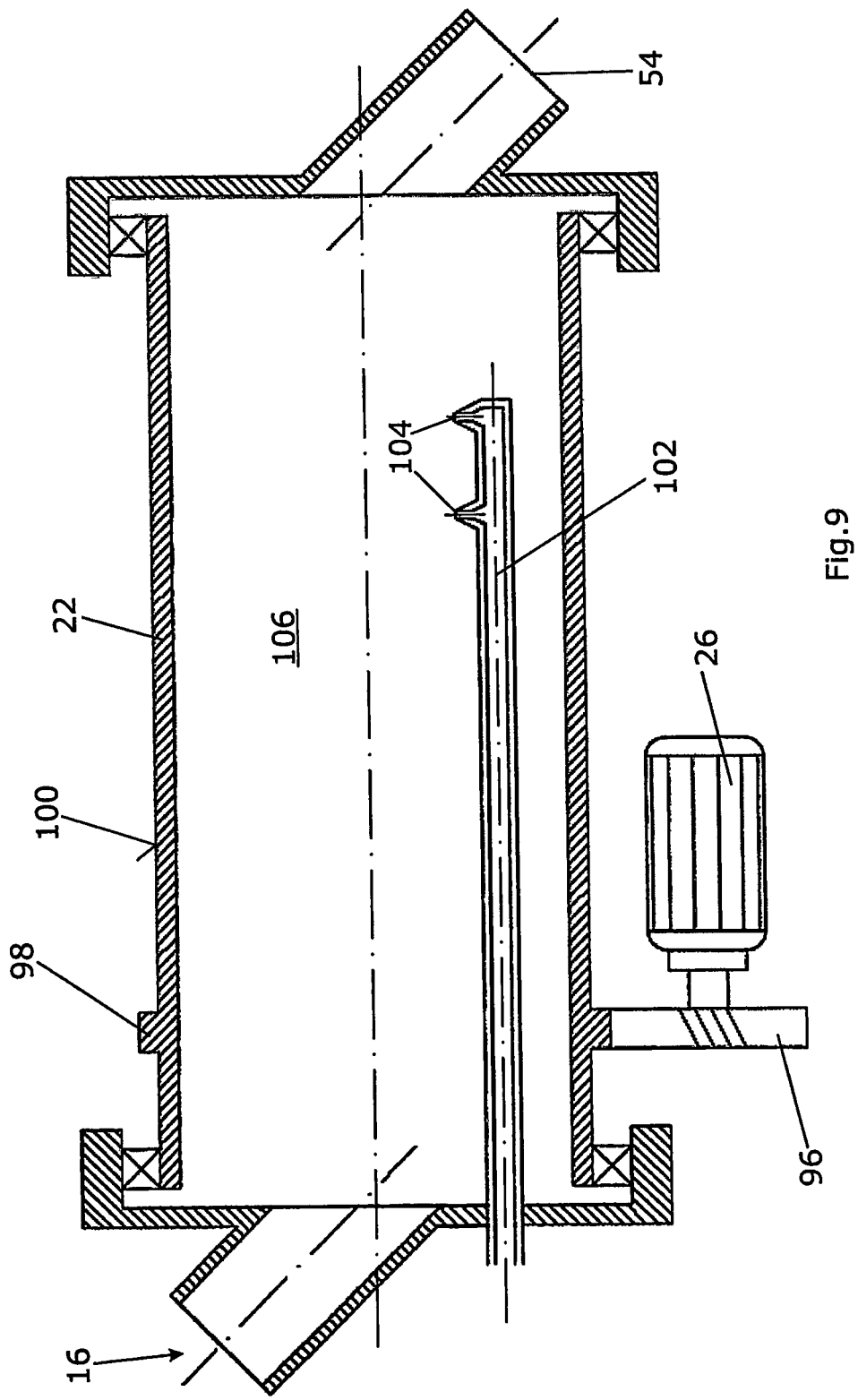

In view of the embodiment shown in FIG. 9, the housing 22 or particularly a cylindrical part of the housing 22 is rotatable. The housing 22 is connected to the motor 26 via a tooth gear 96 and tooths 98 being located on an outer surface 100 of the housing 22. A tube 102 to inject air or liquid through nozzles 104 is inserted in the inner area 106 of the housing 22. In addition to the material in the inner area 106 is mixed by the tube 102.

Figure 10:
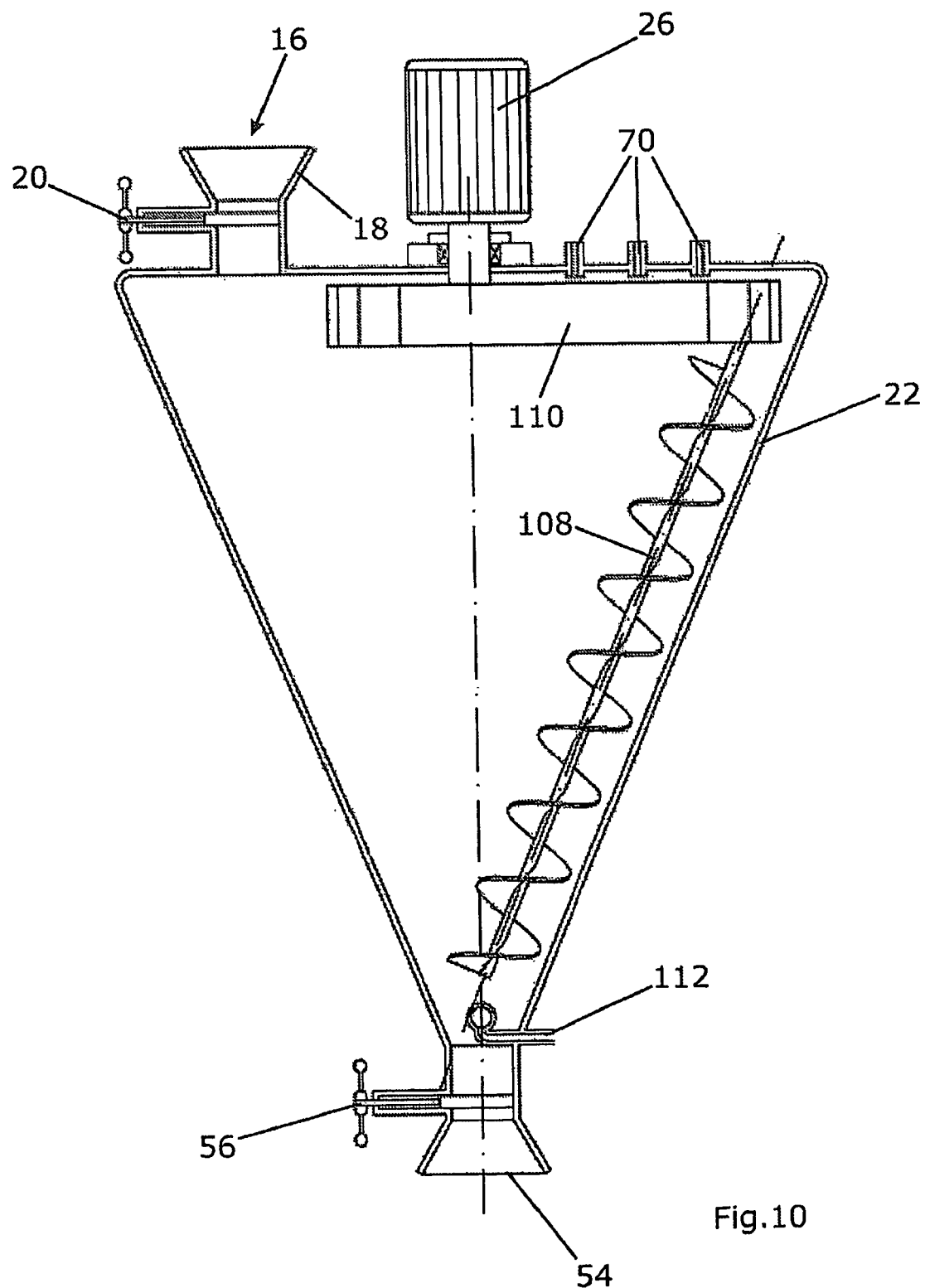
Figure 11:
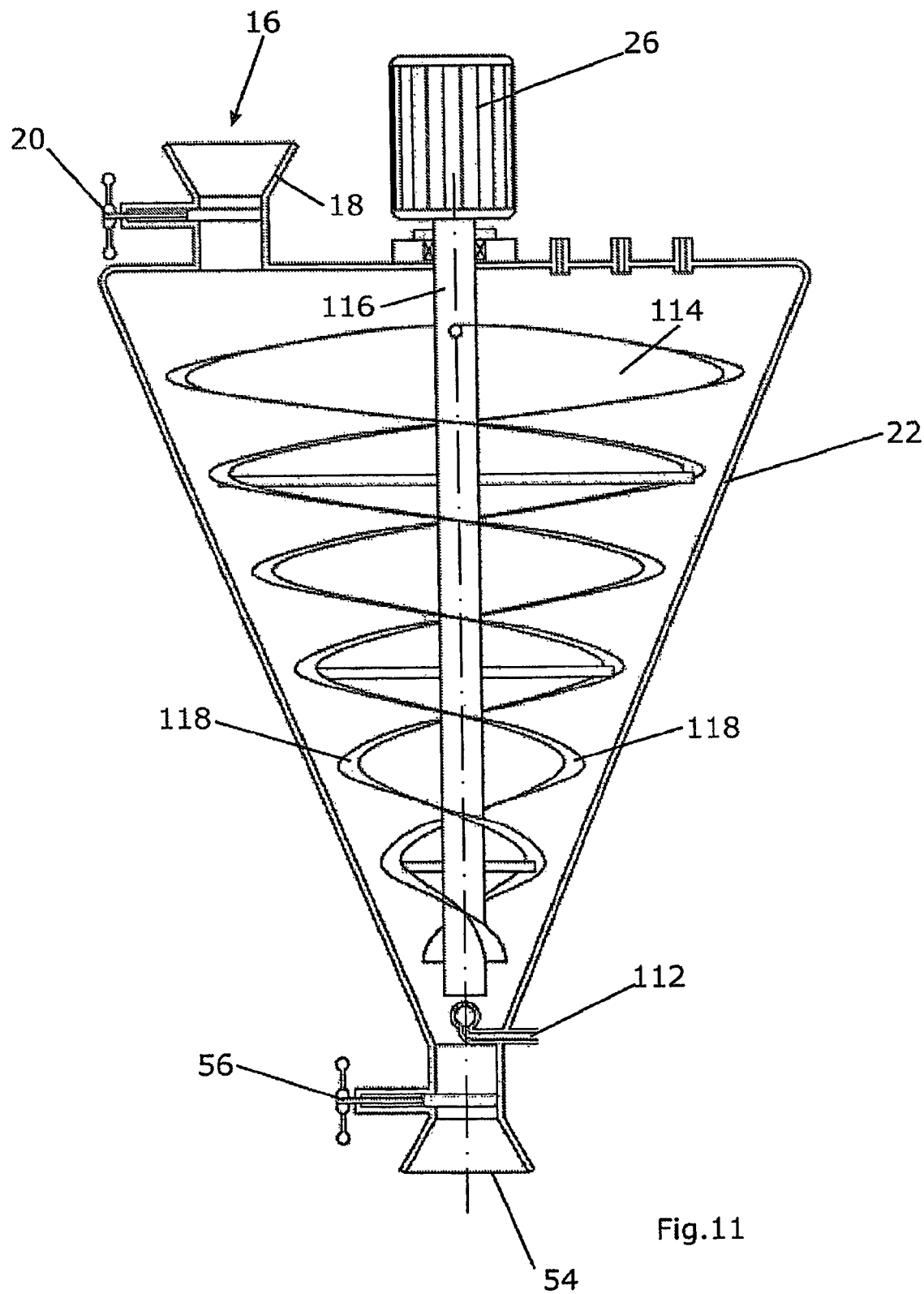

In view of the embodiments shown in FIGS. 10 and 11, the material is transported in the direction of the gravity. To mix the material, a conveying screw 108 is located within the housing 22. In these embodiments (FIG. 10, 11) the housing 22 is conical.

The conveying screw 108 (FIG. 10) is excentrically connected to a driving wheel 110 (FIG. 10) which is connected to the motor 26. By rotating the wheel 110 the conveying screw 108 is rotatable along the inner surface of the housing 22 in addition to the rotation around its own axis. The material within the bioreactor is aerated through the injector 112

In contrast to the embodiment shown in FIG. 10, the embodiment shown in FIG. 11 has a conveying screw 114 with a central access 116 being directly connected to the motor 26. The mixing blades 118 are arranged so that the diameter of the mixing blades 118 is growing with the diameter of the housing 22.

The present invention is more fully described by the following examples. The invention is, however, not limited to these examples.

Materials and Methods

Enzyme activities are in general characterized as unit, "U", meaning µmol product released per min. However, several factors will influence the activity. To allow a comparison between enzyme activities of commercial enzyme products presently used applied in the field of plant material hydrolization with the activities of enzyme mixtures produced by the new fermentation process, described in this application, the enzyme activities were measured using the following tests.

1. Agar Diffusion Assay for Semiquantitative Estimation of Enzyme Activities

Functional principle of the assay: An enzyme probe diffuses through agar, which contains the solid enzyme-specific test substrate. During diffusion the substrate is modified by the enzyme. After a distinct time the reaction is stopped and the degradation halos are visualized by using an appropriate dying procedure or a precipitating (stopping) agent. The diameter of the diffusion-zone is measured. The activity of the unknown probe is quantified by comparison with calibration curves of commercial enzyme activities of similar strains as examined: Cellulase *A. niger* FLUKA 22178, Xylanase *T. viride* FLUKA 95595, Pektinase *A. niger* SERVA 31660, α-Amylase *A. oryzae* SERVA 13448, Lipase *A. niger* FLUKA 62301, Protease *A. oryzae* FLUKA 82463. This method was used to measure the activities of pectinolytic enzymes, xylanases, cellulases, proteases and amylases. The following buffer-solutions were used:

0.1 M phosphate-buffer (pH 5.0): $KH_2PO_4$ (13.50 g) and $Na_2HPO_4.2H_2O$ (0.142 g) were solved in a volume of 1000 ml $H_2O$ and the pH was adjusted to 5 if necessary.

0.1 M phosphate-buffer (pH 6.0): $KH_2PO_4$ (12.10 g) and $Na_2HPO_4.2H_2O$ (1.98 g) were solved in a volume of 1000 ml $H_2O$ and the ph adjusted to pH 6.0 if necessary.

Citrate-phosphate-buffer (pH 5.4): A buffer containing 44.7% 0.1 M citric-acid and 55.3% 0.2 M $Na_2HPO_4$-solution was mixed. The pH was adjusted at pH 5.4 if necessary.

Citrate-phosphate-buffer (pH 6.0): A buffer containing 37.4% 0.1 M citric-acid and 62.6% 0.2 M $Na_2HPO_4$-solution was mixed. The pH was adjusted at pH 6.0 if necessary.

0.1 M Na-Acetate-buffer (pH 5.0): 4.10 g Na-acetate was dissolved in 500 ml $H_2O$ and adjusted to pH 5.0 using concentrated acetic acid.

The following stop reagents and visualizing assay-specific reagents were used:

To stop pectinolytic enzyme reaction: 5 N HCl.

To stop pectinesterase reaction: 10% (w/v) copper-acetate-solution.

To visualize cellulase and xylanase reaction: solutions containing 1 mg/ml Congo-red and 1 M NaCl.

To stop protease reaction: saturated $NH_4SO_4$ solution.

To visualize amylase reaction: Lugol's solution. The Lugol's solution was prepared as follows; 10.0 g potassium-iodide was dissolved in 60 ml $H_2O$. 5.0 g iodide was added and dissolved completely by stirring. The solution was filled up with $H_2O$ to a volume of 100 ml. The solution was stored in the dark. The solution was diluted 1:1000 before use.

Preparation of Enzyme Specific Agar Media:

Pectolytic enzyme agar: To obtain 400 ml agar medium 4 g pectic acid were sterilized in 8 ml 75% ethanol for 10 hours. The resulting pectin-slurry was added to an autoclaved (20 min, 120° C.) solution containing 2% agar in citrate-phosphate-buffer (pH 6). The solution was stirred slowly at 50° C. until the pectic acid was completely dissolved.

Xylanase-agar: 0.2% xylane from birch wood was added to the 0.1 M phosphate-buffer (pH 5.0). 2% agar was added and the solution was autoclaved (120° C., 20 min).

Cellulase-agar: 1.25% carboxymethyl cellulose was added to the 0.1 M phosphate-buffer (pH 5.0). 2% Agar was added and the solution was autoclaved (120° C., 20 min).

Protease-agar: 0.4% casein was added to the 0.1 M phosphate-buffer (pH 6.0). 2% agar was added and the solution was autoclaved (120° C., 20 min).

Amylase-Agar: 1% soluble starch was added to the 0.1 M phosphate-buffer (pH 5.0). 2% agar was added and the solution was autoclaved (120° C., 20 min).

20 ml of each medium were filled in petri dishes. The dishes were closed with parafilm and dried for 48 hours at 30° C. The media could be stored at 7° C. up to 4 weeks.

Experimental conditions: 1 gram of solid enzyme mixture produced by the described method was dissolved in 20 ml water and stirred for 2 hours. The resulting probes were centrifuged (15000 g, 20 min). To obtain sterility the resulting supernatant was filtered through a filter with a pore size of 0.2 µm. Holes with a diameter of 5 mm were punched into the agar with leaving sufficient space between two holes. It was taken care that the walls of the holes were be smooth to obtain an equal diffusion.

In each hole 40 µl enzyme solution were given into. The petri dishes were closed with parafilm and incubated for 20 hours at 30° C.

The agar plates were overlaid with the corresponding stop/visualizing reagents and incubated at room temperature on a shaking dish. It was taken care that the surface of the agar was covered totally by the reagents.

Cellulase- and xylanase-plates: After incubation the plates were overlaid with congo red-solution for 30 min. The remaining congo red-solution was washed away from the surface with the NaCl-solution.

All other plates: After incubation the agar-plates were overlaid with the corresponding reagents and incubated for at least 30 min. The diameter of each diffusion zone was measured. All measurements were done in triplicates.

2. Activity Tests for Glycosidase

Functional principle of the assay: The concentration of reducing sugars can be measured photometrically at $\lambda=510$ nm by following the reduction of 3,5-di-nitrosalicylic acid to 3-amino-5-nitrosalicylic acid.

Solutions

Colour-stop solution: To obtain 1000 ml solution 10 g 3,5-di-nitrosalcylic acid were dissolved in 200 ml $H_2O$. The solution appears yellowish-green. A solution containing 16 g NaOH in 150 ml $H_2O$ was added slowly while the suspension was stirred strongly. The resulting yellowish-orange precipitate was removed by careful heating in a water-bath. 300 g K—Na-tartrate was added in small portions. Finally water was added (total volume 1000 ml). The solution was kept in the dark and was stable for 6 month.

Measurement of enzyme activity: 500 µl probe solution were mixed with 1 ml colour-stop solution in a glass test tube with a volume of 20 ml. The solution was boiled for 12 min. Following boiling the probe was cooled down with ice. 10 ml $H_2O$ were added while agitating vigorously. The absorption of the suspension was measured against water at 510 nm.

Calibration curve: A calibration curve was drawn up using the following solutions:

0  0.0 ml+10.0 ml H$_2$O (0.0 μmol glucose/500 μl solution)
1  0.5 ml 20 mM glucose-solution+9.5 ml H$_2$O (0.5 μmol glucose/500 μl solution)
2  1.0 ml 20 mM glucose-solution+9.0 ml H$_2$O (1.0 μmol glucose/500 μl solution)
3  2.0 ml 20 mM glucose-solution+8.0 ml H$_2$O (2.0 μmol glucose/500 μl solution)
4  3.0 ml 20 mM glucose-solution+7.0 ml H$_2$O (3.0 μmol glucose/500 μl solution)
5  4.0 ml 20 mM glucose-solution+6.0 ml H$_2$O (4.0 μmol glucose/500 μl solution)
6  5.0 ml 20 mM glucose-solution+5.0 ml H$_2$O (5.0 μmol glucose/500 μl solution)

3. Test for Overall Esterase Activity

Functional principle of the assay: The overall activity of hydrolases, especially esterases, can be quantified photometrically by the increase in absorbance at λ=490 nm indicating the hydrolysis of fluorescein-di-acetate (FDA) to fluorescein and acetate.

The following solutions were used: 200 mM PO$_4$-buffer, pH 7.0. For 1 liter buffer 10.52 g NaH$_2$PO$_4$.H$_2$O and 28.24 g K$_2$HPO$_4$ were dissolved in water and the pH adjusted to pH 7.0 with NaOH.

FDA-solution. 20 mg fluorescein-di-acetate were dissolved in 1 ml acetone. The solution was diluted 1:10 with pure acetone before use.

Measurement of enzyme activity: 200 μl test sample (diluted if necessary) was given to 800 μl PO4-buffer, pH 7.0. The reaction was started with the addition of 40 μl FDA-solution. The kinetics of the reaction were monitored continuously at λ=490 nm using a photometer. The maximal increase in absorbance per min was calculated (ΔE/min). For estimation of activity a calibration curve with fluorescein was used.

4. Activity Test for Lipase:

Functional principle of the lipase test: The release of p-nitrophenole (pNP) from pNP-butyrate is measured photometrically at λ=410 nm The following solutions were used:

50 mM Na-phosphat-buffer, pH 7.0; 3.11 g NaH$_2$PO$_4$.H$_2$O were dissolved in 450 ml H$_2$0. The pH was adjusted to pH 7.0 with 5 N NaOH.

Reaction buffer: To 450 ml 50 mM Na-phosphate-buffer, pH 7.0 0.5 g gummi Arabicum and 2 g Triton® X-100 were given.

pNPB-solution: 30 mg pNP-butyrate (PNPB) were dissolved in 10 ml isopropanole.

Measurement of enzyme activity: 100 μl test sample (diluted if necessary) were given to 810 μl reaction buffer. The reaction was started with the addition of 90 μl pNPB-solution. The kinetics of the reaction were monitored continuously at λ=410 nm using a photometer. The maximal increase in absorbance per min was calculated (ΔE/min). For estimation of activity a calibration curve with p-nitrophenole was used.

5. Enzyme Activity Testing of Commercial Products.

Based on enzyme activity assays enzymes mentioned, three commercial enzymes optained from Novozym show the following activities at 30° C.:

| | Enzyme activity in [U/ml] | | |
|---|---|---|---|
| | Viscozyme L | Celluclast | Ultrazyme |
| FDA | 6300 | 381 | 637 |
| Pektinase | 10.37 | 0.59 | 7.7 |
| Cellulase | 90 | 43 | 68 |
| Xylanase | 7 | 370 | 180 |
| Protease | 2 | 0 | 0 |
| Amylase | 0.7 | 0.1 | 3 |
| Lipase | 25 | 26 | 15 |

EXAMPLES

Continuous production of specific hydrolase mixtures with an inductively optimized preculture for the saccharification of exhausted sugar beet chips.

Raw materials from naturally renewable resources usually contain significant amounts of hardly degradable biopolymers, such as lignocellulose, cellulose, hemicelluloses (xylan), pectin, cutin etc. These biopolymers which are obtained in important quantities and form the major component or an important fraction, for example, for sugar beet or sugar cane scraps, and are obtained in large quantities in agriculture could not be utilized to date, or only so in a less than optimum way. In addition, their use as a fodder is in part restricted by legal regulations.

Example 1

Two-Phase Culture for Producing Hydrolase Mixtures for a Subsequent Enzymatic Extraction Process for Exhausted Sugar Beet Chips A. Enzyme Production:

In a two-phase culture with an upstream inductive preculture, for preparing the precultures, ground (Retsch centrifugal mill: about 250 μm sieve mesh width) press beet chips/rapeseed meal, at 2% each, was added into 2% agar suspension+ 0.5% yeast extract (w/v), and after autoclavation, poured into Petri dishes (about 30 ml per Petri dish/9 cm diameter). After cooling and drying for about 3 days at room temperature, the preculture substrates are inoculated with *Penicillium chrysogenum, Eurotium amstelodami, Aspergillus niger, Aspergillus tubingiensis* and *Neurospora* spec. Thus, a round piece of inoculum is punched out of one of each grown agar culture of the respective fungus by means of a cork borer and placed into a previously punched hole in the inoculation plate. The inductive preculture phase at about pH 5-6 and at a temperature of about 30° C. lasts for about 4-6 days. Depending on the amount of the phase 1 culture to be inoculated, the content of preculture plates is disintegrated in a striking work (e.g., Waring blender) and mixed into target substrate 1 (press beet chips), and under suitable culturing parameters, a mixed culture is selectively produced in the preferred screw reactor mentioned to produce the desired hydrolytic enzymes (total moisture content: 50%, pH 5-6, about 30° C.). In the second process step, by adding target substrate 2 (exhausted and comminuted sugar beet chips), a further conditioned and optimized mixed culture is selectively produced with a spectrum of hydrolytic enzymes that is adapted to the target substrate sugar beet chips (total moisture content: 40%, pH 5-6, about 30° C.).

B. Extraction of Sugar Beet Chips:

The entire enzyme-containing fermentation matter obtained in A. is continuously added to the substrate to be saccharified, i.e., exhausted sugar beet chips; →saccharification step (pH 5-6, about 30° C.). During the saccharification step, which is performed with exclusion of air to prevent the fungi from further growing with the undesirable metabolization of the sugars, the active enzymes digest the vegetable residual polymers.

With the enzyme cocktail produced according to step A. of this Example with an inductively optimized preculture, the total sugar yield in a laboratory experiment could be increased by 10% as compared to the mixture of enzymes produced without an inductively optimized preculture.

Example 2

Hydrolysation of Grass Silage

A. Enzyme Production:

Two *Aspergillus* strains (*niger, tubingensis*) and one *Neurospora* strain (*intermedia*) were cultivated in a bioreactor according to FIG. 1 as follows: 1 kg rape extraction material was adjusted to a water activity of 0.98. The substrate was inoculated with $10^7$ conidiospores/g substrate of *A. niger*, $10^8$ conoidiospores/g substrate of *A. tubingensis* and $10^8$ conoidiospores/g substrate of *Neurospora* intermedia. After 3 days of cultivation 200 g grass silage, which was cut into pieces smaller than 10 mm, as inducing target substrate was added. The water activity was adjusted to 0.99 by adding water and the mixture was in addition inoculated with $10^8$ conidiospores of a *Trichoderma* strain (*atroviride*). After another two days the fermentation was stopped, the fermentation product was dried and homogenized using the above mention enzyme assays the homogenized product showed following activities per g dried material: Cellulase 80; Xylanase 107; Pectinase 0; Amylase 1; Protease 1; Upase 14; unspecific esterase (FDA) 1107.

B. Hydrolysation of Grass Silage:

5 g grass silage were dissolved in 50 ml water. 0.2 g of dried enzyme mixture with the above mentioned activities were added. The culture was shaken on a rotatory shaker at 30° C. for 24 hours. 1 ml probes were taken after 10 min 1 hour, 2 hours, 6 hours and 24 hours. Sugar concentrations in the probes were measured using DNS-test (see above). After 24 h the probe is filtered through filter paper. The filter paper is dried at 105° C. until constant weight. Parallel probes were treated in the same way with 0.2 ml of the Novozyme enzymes "Viscozym", "Ultrazyme" and "Celluclast". All experimentals were done in duplicates.

Figure 12:
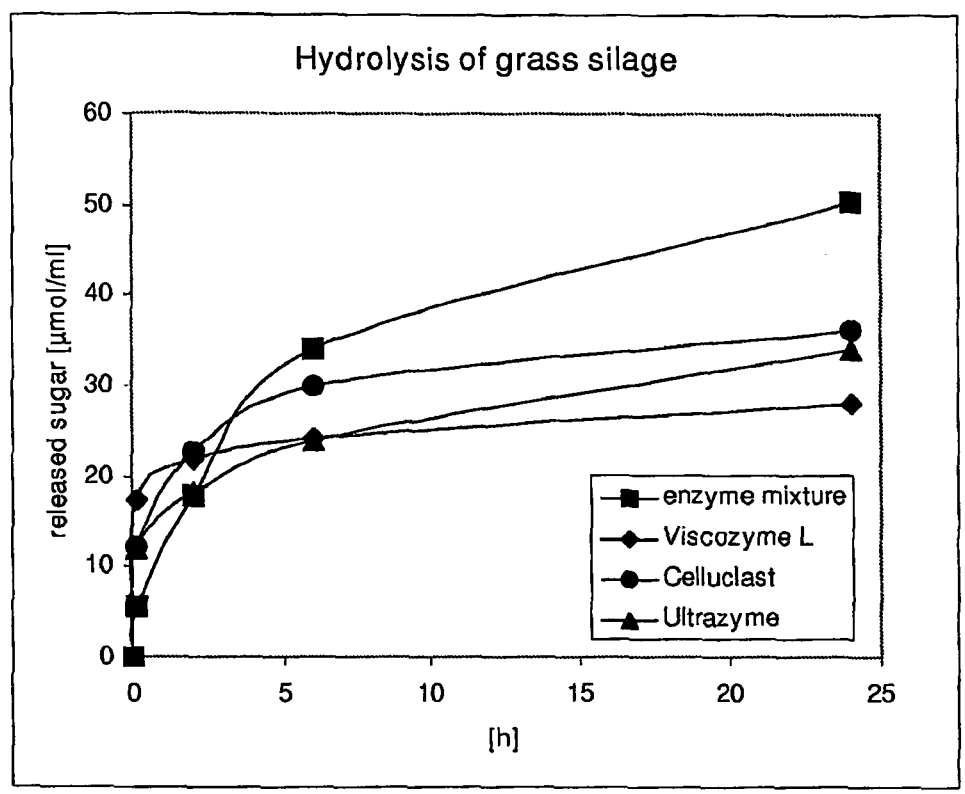
FIG. 12 shows the sugar release when hydrolyzing grass silage according to Example 2.

C. Results:

As can be seen from FIG. 12 the adapted enzyme mixture hydrolysed grass silage as fast as the commercial enzymes within two and six hours. After 24 h the sugar polymers were completely hydrolysed by the adapted enzyme mixture, whereas the values of the commercial enzymes were 40% lower.

Figure 13:
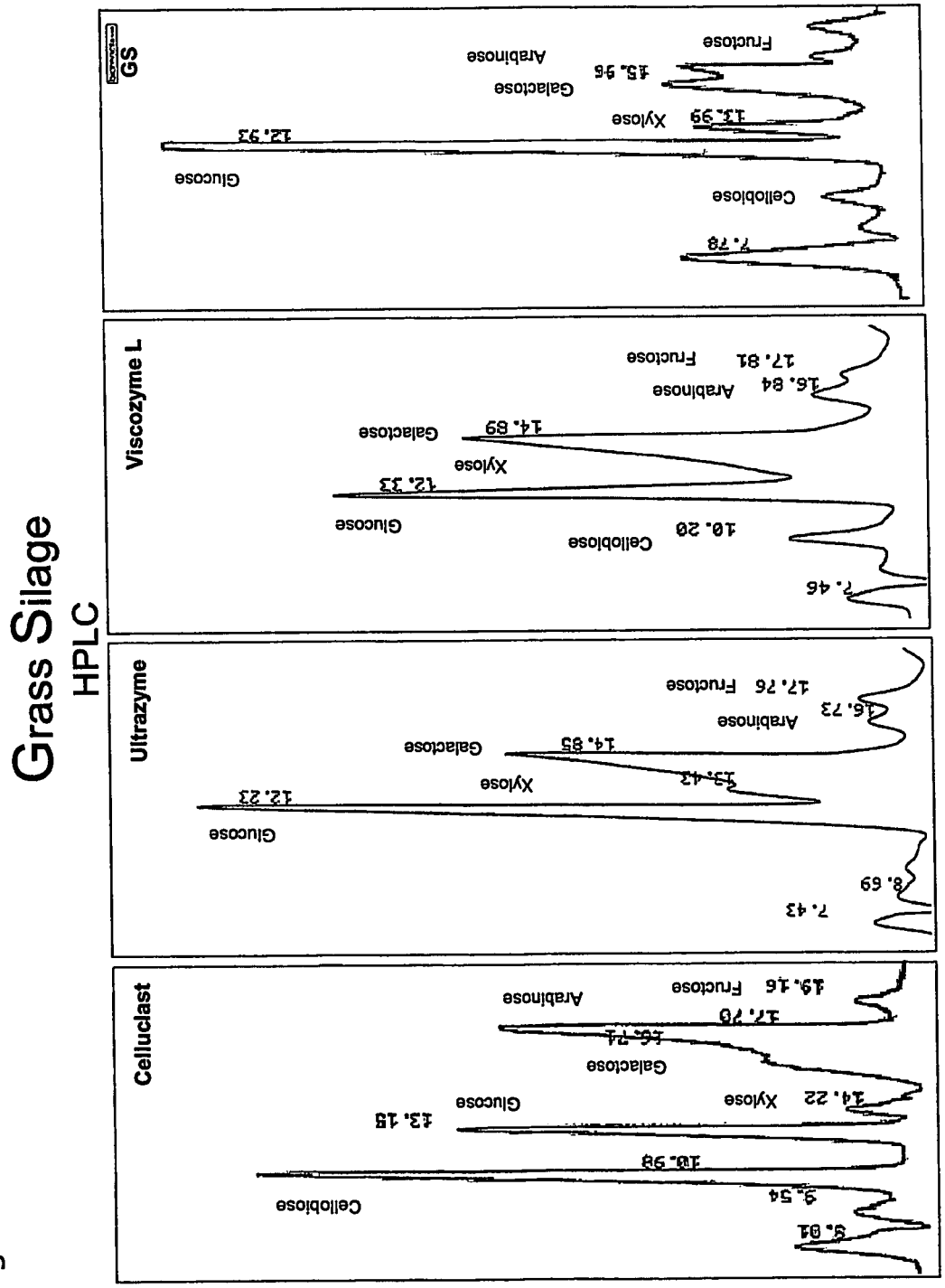
FIG. 13 shows the HPLC analysis of sugar components after 24 hour hydrolization of grass silage according to Example 2.

Moreover, as can be seen from FIG. 13 and Tables 1 and 2, HPLC-analysis of sugar components released after 24 hour hydrolyzation indicates that the adapted enzyme mixture (GS) is able to release a broad spectrum of sugar components from grass silage.

TABLE 1

Calculation of released sugars based on HPLC peaks

|  | Cellulast | CS [mg/50 ml] |
|---|---|---|
| Glucose | 60.6 | 166.6 |
| Galactose/Arabinose | 108.1 | 81.0 |

TABLE 1-continued

Calculation of released sugars based on HPLC peaks

|  | Cellulast | CS [mg/50 ml] |
|---|---|---|
| Xylose | 7.3 | 25.0 |
| Cellobiose | 85.0 | n.d. |

With the adapted enzyme mixture 46% of the grass silage were hydrolysed.

TABLE 2

|  | Enzyme mixture | Control* |
|---|---|---|
| Fresh grass silage | 5 g | 5 g |
| Dry weight | 2.19 g | 2.19 g |
| Residual of first filtration | 1.2921 g | 1.6206 |
| Grade of degradation | 41% | 26% |
| Residual of second filtration | 1.1826 | 1.5768 g |
| Grade of degradation | 46% | 28% |

*heat inactivated enzyme mixture

D. Hydrolysation Product as Substrate for Biogas and Ethanol Production:

The following experiments were done to proof the principle suitability of the released substances of grass silage for production of biogas and bioethanol. The results are summarized in Table 3.

Biogas:

30 g grass silage, 1.2 g enzyme mixture and 300 ml water were stirred for 24 hours at 30° C. After 24 hours the total probe was filtered through filter paper. 100 ml of the permeate were given to 200 ml sewage slugde under anaerobic conditions. The biogas produced was collected for 24 hours. As a control the experiment was performed without addition of enzymes.

Figure 14:
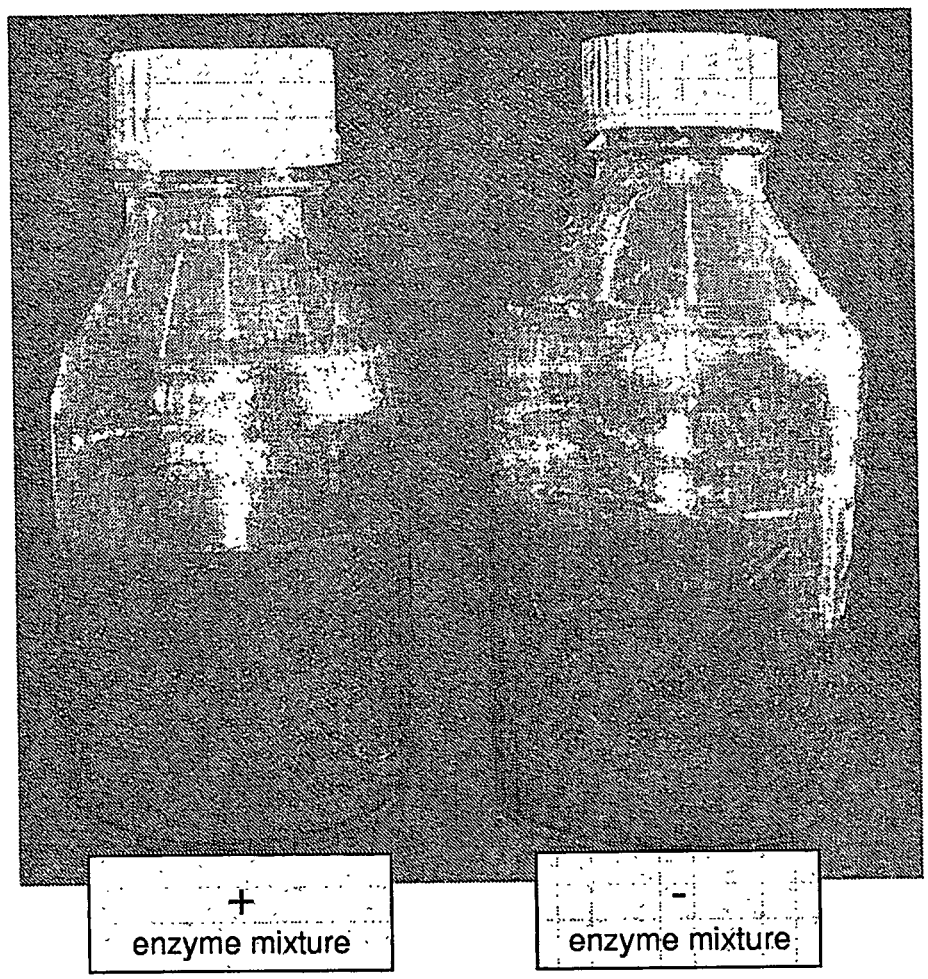
FIG. 14 shows the degradation of grass silage with and without the enzyme according to Example 2.

Bioethanol:

30 g grass silage, 1.2 g enzyme mixture and 300 ml water were stirred for 24 hours at 30° C. After 24 hours the total probe was filtered through filter paper. 100 ml of the permeate were given to 200 ml water and 5 g bakers yeast (*Saccharomyces cerevisiae*) and stirred under anaerobic conditions. The bioethanol produced was measured after 24 hours incubation. As a control the experiment was performed without addition of enzymes. The results are summarized in Table 3. Moreover, FIG. 14 shows the visual degradation of grass silage after 24 hours incubation before filtration.

TABLE 3

|  | Enzyme treated | Control |
|---|---|---|
| Produced biogas (ml) | 260 | 120 |
| Produced bioethanol (g/l) | 1 | 0.25 |

Example 3

Hydrolysation of Sugar Beet Pulp

A. Enzyme Production:

Two *Aspergillus* strains (*niger, tubingensis*) were cultivated in a bioreactor according to FIG. 1 as follows: 1 kg rape extraction material was adjusted to a water activity of 0.99. The substrate was inoculated with $10^7$ conidiospores/g substrate of *A. niger* and $10^8$ conoidiospores/g substrate of *A. tubingensis*. After 3 days of cultivation 200 g sugar beet pulp as inducing target substrate was added. The water activity was adjusted to 0.96 by forced aeration and the mixture was in addition inoculated with $10^7$ conidiospores of *Neurospora intermedia*. After another three days the fermentation was stopped, the fermentation product was dried and homogenized.

Using the above mention enzyme assays the homogenized product showed in following activities per g dried material: Cellulase 94; Xylanase 183; Pectinase 4; Amylase 1; Protease 1; Upase 19; unspecific esterase (FDA) 1430.

B. Hydrolysation of Sugar Beet Pressed Pulp:

7.5 g sugar beet pulp were dissolved in 25 ml water. 0.2 g of dried enzyme mixture with the above mentioned activities were added. The culture was shaken on a rotatory shaker at 30° C. for 24 hours. 1 ml probes were taken after 10 min, 1 hour, 2 hours, 6 hours and 24 hours. Sugar concentration in the probes were measured by using the DNS-test (see above). After 24 hours the probe was filtered through filter paper. The filter paper was dried at 105° C. until constant weight. Parallel probes were treated in the same way using 0.2 ml of the Novozyme Enzymes "Viscozyme L", "Ultrazyme" and "Celluclast". All experimentals were done two fold.

Figure 15:
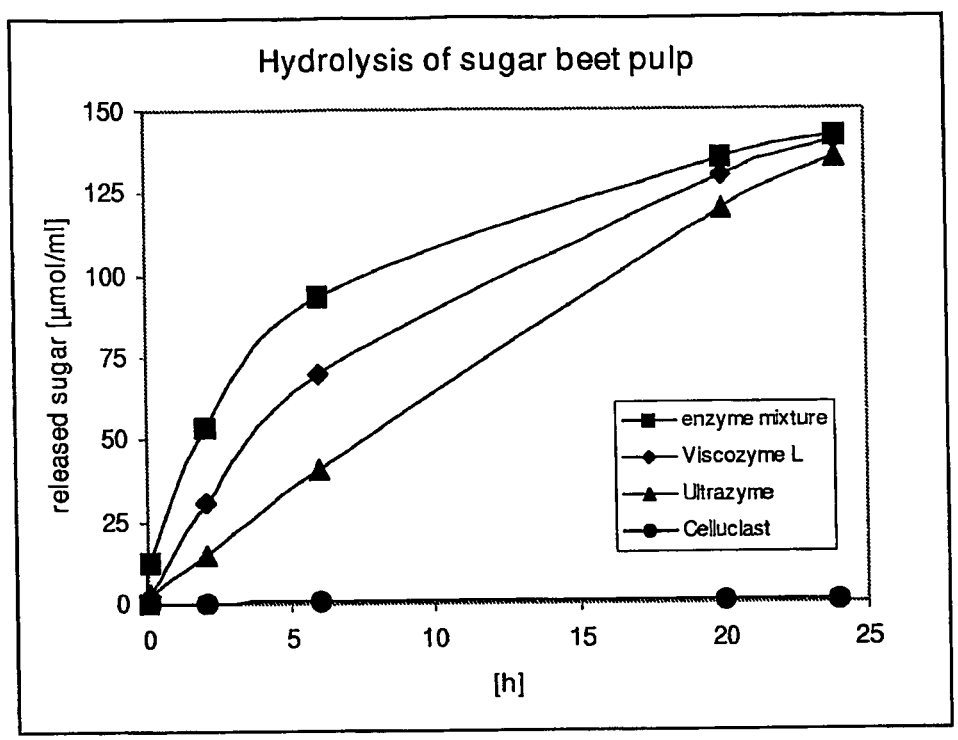
FIG. 15 shows the sugar release when hydrolyzing sugar beet pulp according to Example 3.

C. Results:

As can be seen from FIG. 15, the adapted enzyme mixture hydrolysed sugar beet pulp two times faster within the first two hours. After 24 h the sugar polymers were completely hydrolysed. Total hydrolysis could be obtained also by "Viscozyme" and "Ultrazyme" whereas "Celluclast" had no effect at all.

Figure 16:
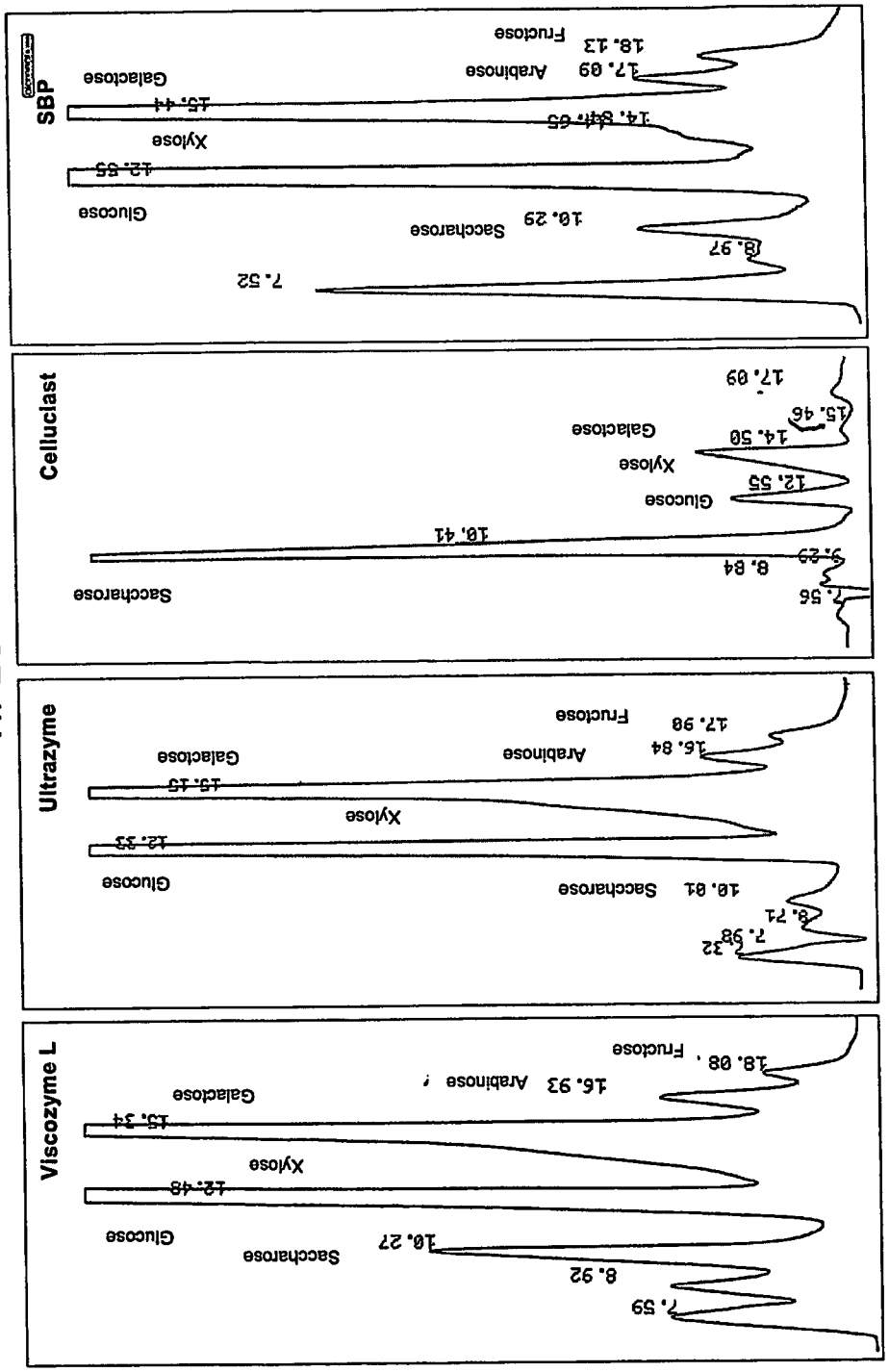
FIG. 16 shows the HPLC analysis of sugar components after 24 hour hydrolization of sugar beet pulp according to Example 3.

Moreover, as can be seen from FIG. 16 and Tables 4 and 5, HPLC-analysis of sugar components released after 24 hour hydrolysation demonstrated that the adapted enzyme mixture (SBP) is able to release a broad spectrum of sugar components. With the adapted enzyme mixture 81% of the sugar beet pulp could be hydrolysed.

TABLE 4

Calculation of released sugars based on HPLC peaks

|  | Viscozyme L | SBP [mg/50 ml] |
| --- | --- | --- |
| Glucose | 325.4 | 452.0 |
| Xylose/Galactose | 324.4 | 328.2 |
| Saccharose | 74.4 | 18.0 |
| Arabinose | 35.8 | 36.1 |
| Fructose | 15.3 | 26.0 |

TABLE 5

Degradation of sugar beet pulp

|  | Enzyme mixture | Control* |
| --- | --- | --- |
| Fresh sugar beet pulp | 7.5 g | 7.5 g |
| Dry weight | 2.065 g | 2.065 g |
| Residual of first filtration | 0.598 g | 1.528 g |
| Grade of degradation | 71% | 26% |
| Residual of second filtration | 0.392 g | 1.507 g |
| Grade of degradation | 81% | 27% |

*heat inactivated enzyme mixture

D. Hydrolysation Product as Substrate for Biogas and Ethanol Production:

The following experiments were done to proof the principle suitability of the released substances of sugar beet pulp for production of biogas and bioethanol. The results are summarized in Table 3.

Biogas:

90 g sugar beet pulp, 2.4 g enzyme mixture and 300 ml water were stirred for 24 hours at 30° C. After 24 hours the total probe was filtered through filter paper. 100 ml of the permeate were given to 200 ml sewage sludge under anaerobic conditions. The biogas produced was collected for 24 hours. As a control the experiment was performed without addition of enzymes.

Figure 17:
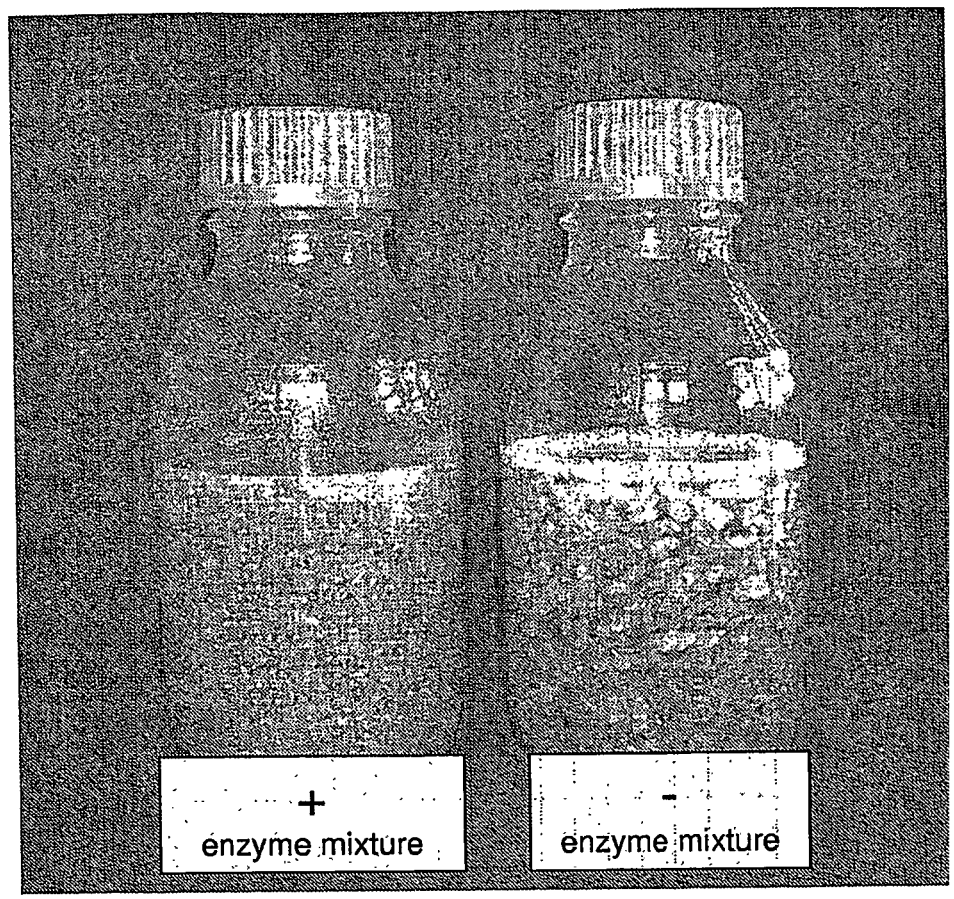
FIG. 17 shows the degradation of sugar beet pulp with and without the enzyme composition according to Example 3.

Bioethanol:

90 g sugar beet pulp, 2.4 g enzyme mixture and 300 ml water were stirred for 24 hours at 30° C. After 24 hours the total probe was filtered through filter paper. 100 ml of the permeate were given to 200 ml water and 5 g bakers yeast (*Saccharomyces cerevisiae*) and stirred under anaerobic conditions. The bioethanol produced was measured after 24 hours incubation. As a control the experiment was performed without addition of enzymes. The results are summarized in Table 6. Moreover, FIG. 17 shows the visual degradation of sugar beet pulp after 24 hours incubation before filtration.

TABLE 6

|  | Enzyme treated | Control |
| --- | --- | --- |
| Produced biogas (ml) | 800 | 200 |
| Produced bioethanol (g/l) | 2.5 | 0.5 |

Example 4

Hydrolysation of Corn Silage

A. Enzyme Production:

Two *Aspergillus* strains (*niger, tubingensis*) and one *Neurospora* strain (*intermedia*) were cultivated in a bioreactor according to FIG. 1 as follows: 1 kg rape extraction material was adjusted to a water activity of 0.98. The substrate was inoculated with $10^7$ conidiospores/g substrate of *A. niger*, $10^8$ conoidiospores/g substrate of *A. tubingensis* and $10^8$ conoidiospores/g substrate of *Neurospora intermedia*. After 3 days of cultivation 200 g corn silage, which was cut into pieces smaller than 10 mm, as inducing target substrate was added. The water activity was adjusted to 0.99 by adding water and the mixture was in addition inoculated with $10^8$ conidiospores of another *Aspergillus* strain (*oryzae*). After another two days the fermentation was stopped, the fermentation product was dried and homogenized. Using the above mention enzyme assays the homogenized product showed the following activities per g dried material: Cellulase 40; Xylanase 444; Pectinase 5; Amylase 150; Protease 1; Lipase 1; unspecific esterase (FDA) 777.

B. Hydrolysation of Corn Silage:

5 g corn silage were dissolved in 50 ml water. 0.2 g of dried enzyme mixture with the above mentioned activities were added. The culture was shaken on a rotatory shaker at 30° C. for 24 hours. 1 ml probes were taken after 10 min 1 hour, 2 hours, 6 hours and 24 hours. Sugar concentrations in the probes were measured by using DNS-test (see above). After 24 hours the probe was filtered through filter paper. The filter paper was dried at 105° C. until constant weight. Parallel probes were treated in the same way with 0.2 ml of the Novozyme enzymes "Viscozyme L", "Ultrazyme" and "Celluclast". All experimentals were done in duplicates.

Figure 18:
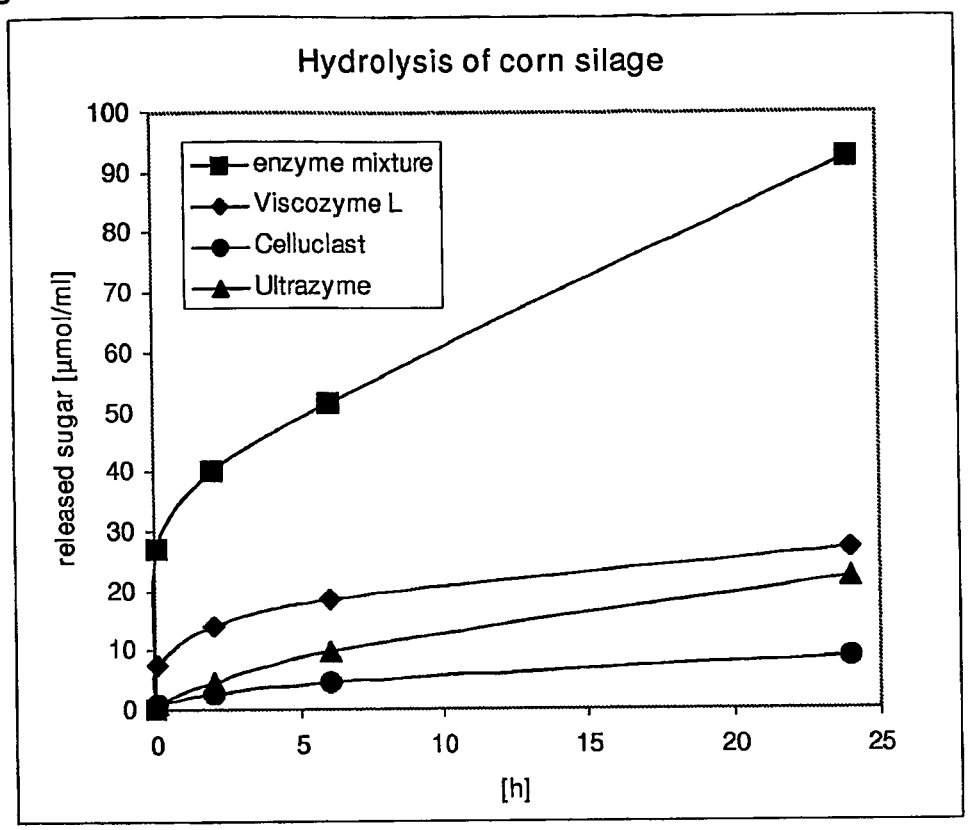
FIG. 18 shows the sugar release when hydrolyzing corn silage according to Example 4.

C. Results:

As can be seen from FIG. 18, the adapted enzyme mixture hydrolysed corn silage 3 times faster within two and six hours. After 24 h the sugar polymers are completely hydrolysed. The tested known commercial enzymes of Novozym had only a small effect.

Figure 19:
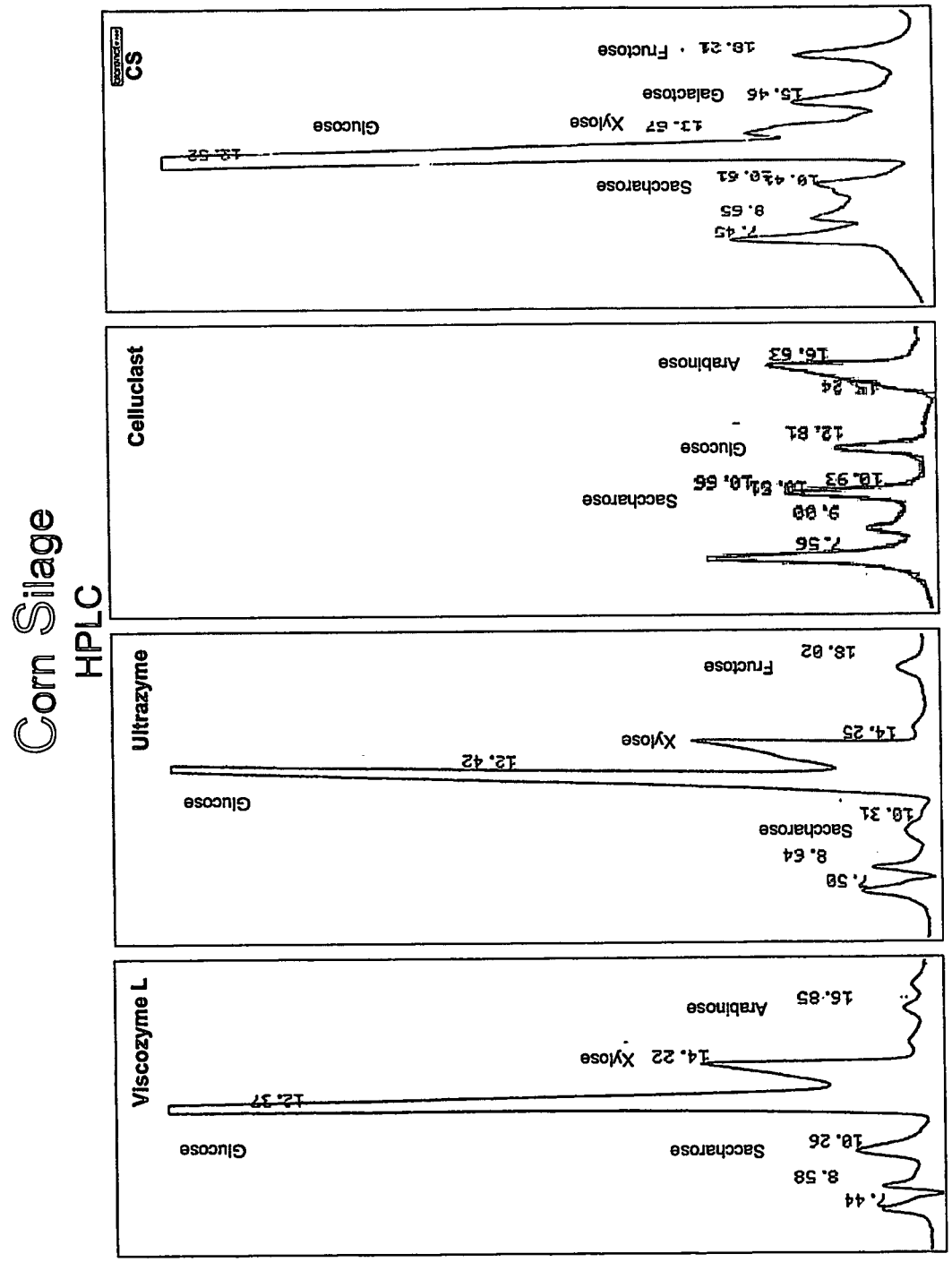
FIG. 19 shows the HPLC analysis of sugar components after 24 hour hydrolization of corn silage according to Example 4.

Moreover, as can be seen from FIG. 19 and Tables 7 and 8, HPLC-analysis of sugar components released after 24 hours hydrolysation demonstrated that the adapted enzyme mixture (CS) could release a broad spectrum of sugar components. With the adapted enzyme mixture 52% of the corn silage were hydrolysed.

TABLE 7

Calculation of released sugars based on HPLC peaks

|  | Viscozyme L | CS |
|---|---|---|
| Glucose | 163 mg/50 ml | 524.5 mg/50 ml |
| Xylose | 56.8 mg/50 ml | 45.1 mg/50 ml |
| Saccharose | 1.2 mg/50 ml | 2.7 mg/50 ml |
| Fructose | n.d. | 23.4 mg/50 ml |
| Galactose | n.d. | 24.6 mg/50 ml |

TABLE 8

Degradation of corn silage

|  | Enzyme mixture | Control* |
|---|---|---|
| Fresh corn silage | 5 g | 5 g |
| Dry weight | 1.79 g | 1.79 g |
| Residual of first filtration | 0.9308 g | 1.3246 g |
| Grade of degradation | 48% | 26% |
| Residual of second filtration | 0.8592 g | 1.3067 g |
| Grade of degradation | 52% | 27% |

*heat inactivated enzyme mixture

D. Hydrolysation Product as Substrate for Biogas and Ethanol Production:

The following experiments were done to proof the principle suitability of the released substances of corn silage for production of biogas and bioethanol The results are summarized in Table 9.

Biogas:

30 g corn silage, 1.2 g enzyme mixture and 300 ml water were stirred for 24 hours at 30° C. After 24 hours the total probe was filtered through filter paper. 100 ml of the permeate was given to 200 ml sewage sludge under anaerobic conditions. The biogas produced was collected for 24 hours. As a control the experiment was performed without addition of enzymes.

Figure 20:
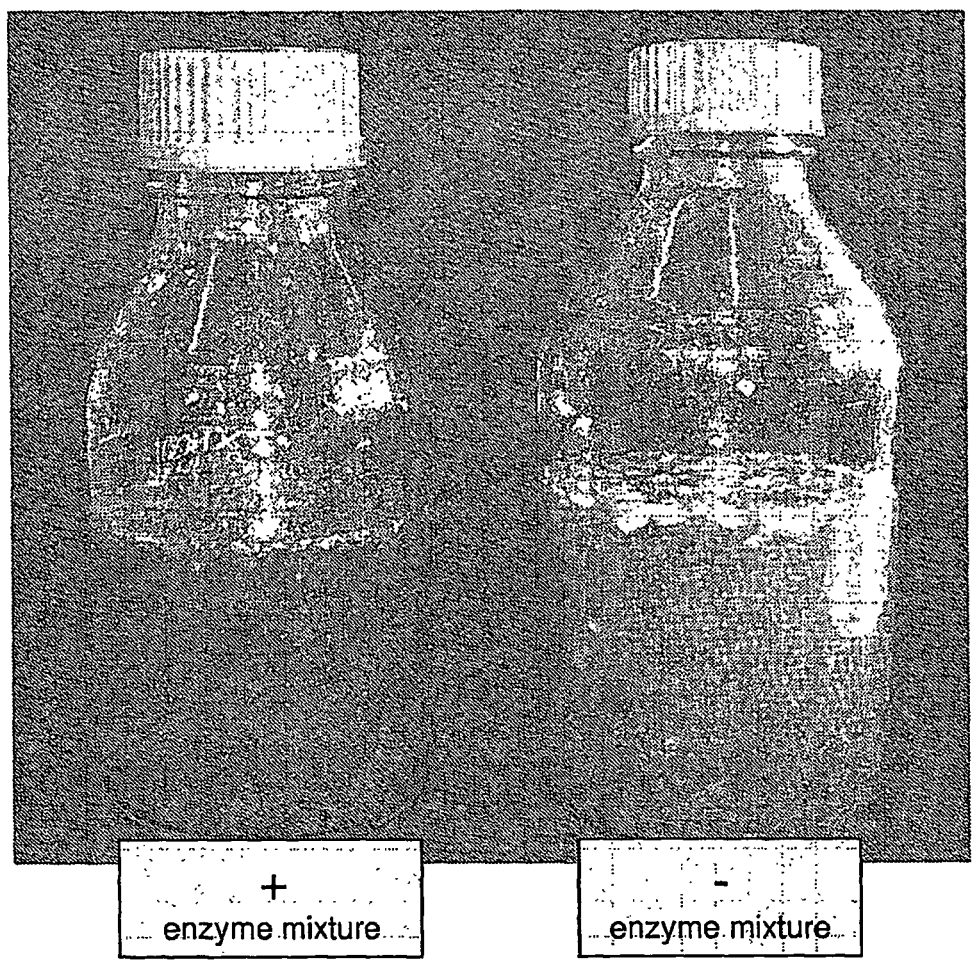
FIG. 20 shows the degradation of corn silage with and without the enzyme according to Example 4.

Bioethanol:

30 g corn silage, 1.2 g enzyme mixture and 300 ml water were stirred for 24 hours at 30° C. After 24 hours the total probe was filtered through filter paper. 100 ml of the permeate was given to 200 ml water and 5 g bakers yeast (*Saccharomyces cerevisiae*) and stirred under anaerobic conditions. The bioethanol produced was measured after 24 hours incubation. As a control the experiment was performed without addition of enzymes. Moreover, FIG. 20 shows the visual degradation of corn silage after 24 hours incubation before filtration.

TABLE 9

|  | Enzyme treated | Control |
|---|---|---|
| Produced biogas (ml) | 340 | 130 |
| Produced bioethanol (g/l) | 1.5 | 0.5 |

The invention claimed is:

1. A semisterile culture method for producing an enzyme mixture by a mixed culture of microorganisms optimized for the degradation of one or more target substrates, the method comprising
   (a) cultivating an inoculum of a mixed culture of microorganisms in a solid-phase bioreactor with one or more solid inducer substrates, wherein at least two microorganisms are selected from *A. niger*, *A. tubingensis* and *Neurospora intermedia*, and wherein at least one solid inducer substrate is rape extraction material,
   (b) controlling the water activity during the cultivation to force selection pressure on the growing mixed culture of microorganisms; and
   (c) adding one or more solid target substrates to the mixed culture in the bioreactor at one or more later time points during the course of the cultivation, wherein the solid target substrates are different from the inducer substrates and whereby producing the enzyme mixture optimized for the degradation of one or more target substrates.

2. The method according to claim 1, wherein the inoculum of a mixed culture is obtained by culturing a solid or liquid preculture of mixed microorganisms adapted to solid or liquid substrates.

3. The method of claim 1, wherein the water activity is controlled by the addition of water and its removal by evaporation.

4. The method of claim 3, wherein the water activity is between 0.85 and 0.99.

5. The method of claim 1, wherein the method is performed in a continuous manner or in a step-wise manner with one or more process cycles.

6. The method of claim 1, wherein the enzyme mixture is suitable applied as such.

7. The method of claim 1, wherein the enzyme mixture is separated from the culture to obtain a liquid enzyme cocktail.

8. The method of claim 1, wherein the enzyme mixture is suitable for the saccharification of natural polysaccharide substrates or for the degradation of vegetable, animal or microbial polymers.

9. The method of claim 1, further comprising supplementing the enzyme mixture with commercially available enzymes.

10. The method of claim 1, wherein the enzyme mixture is suitable for fermentation under essentially anaerobic or anaerobic conditions.

11. The method claim 1, wherein the enzyme mixture is a hydrolase cocktail, oxidoreductase cocktail, or a combination thereof.

12. The culturing method of claim 1, wherein the enzyme mixture is directly supplied to the downstream processes.

13. The culturing method of claim 1, wherein the enzyme mixture is transferred to another solid state process operation in which the substrate which is to be fermented later is selectively utilized for producing enzymes and at least partially hydrolyzed.

14. The method of claim 1, wherein the methods are performed in screw reactor, drum reactor, tower reactors trickling film reactor, solid-state air-lift reactor, horizontal mixer, or vertical mixer.

15. The method of claim 14, wherein the semisterile culture is performed according to the principle of screw conveying, pressure screw conveying, or conveying belt transport.

16. The method of claim 14, wherein the semisterile culture is modified or in a cascade form.

17. The method of claim 14, wherein the semisterile culture is performed (a) in a screw reactor either singly or arranged in a cascade form; or (b) in special solid-state air-lift reactors; or (c) as batch cultures, fed-batch cultures or continuously.

18. The method of claim 1, further comprising conservation of the obtained semisterile culture by decreasing the water activity during the fermentation process, wherein water activity is decreased by air flow through the substrate or by a final drying step.

19. The method of claim 18, wherein the final drying step is in a fluidised bed or belt dryer.

20. The method of claim 1, wherein a leaching of the produced enzyme mixture is carried out by moving or stirring it with water, buffer, detergent/water or detergent/buffer solutions for 30 min to 2 hours and wherein the produced enzyme mixture is filtered and the filtrate is further used as a solvent for additional leaching cycles for receiving a highly concentrated enzyme slurry.

21. The method of claim 20, wherein the filtrate is used as a solvent for up to 10 additional leaching cycles.

22. An enzyme mixture produced by a process comprising:

(a) cultivating an inoculum of a mixed culture of microorganisms in a solid-phase bioreactor with one or more solid inducer substrates, wherein at least two microorganisms are selected from *A. niger, A. tubingensis* and *Neurospora intermedia*, and wherein at least one solid inducer substrate is rape extraction material, (b) controlling the water activity during the cultivation to force selection pressure on the growing mixed culture of microorganisms; and (c) adding one or more solid target substrates to the mixed culture in the bioreactor at one or more later time points during the course of the cultivation, wherein the solid target substrates are different from the inducer substrates; thereby producing the enzyme mixture.

23. The method according to claim 1, wherein the culturing is performed in a bioreactor comprising a fermentation module for the fermentation of substrates under selection pressure whereby the fermentation module comprises regulation means to adjust a fermentation environment, a feeding means being connected to the fermentation module to feed the substrate, an induction module for adding reagents to the fermentation media, a harvesting module comprising outlet means and a conveying means to convey the media from the fermentation module through the induction module to the harvesting module.

* * * * *